(12) United States Patent
Ito

(10) Patent No.: US 11,221,299 B2
(45) Date of Patent: Jan. 11, 2022

(54) ULTRA-HIGH-SENSITIVE ASSAY OF PROTEIN AND NUCLEIC ACID AND KIT, AND NOVEL ENZYME SUBSTRATE

(71) Applicants: Etsuro Ito, Sapporo (JP); Satoshi Watabe, Ito (JP); Toshiaki Miura, Sapporo (JP); Teruki Yoshimura, Sapporo (JP)

(72) Inventor: Etsuro Ito, Sapporo (JP)

(73) Assignees: Satoshi Watabe, Shizuoka (JP); Toshiaki Miura, Hokkaido (JP); Teruki Yoshimura, Hokkaido (JP)

( * ) Notice: Subject to any disclaimer, the term of this patent is extended or adjusted under 35 U.S.C. 154(b) by 336 days.

(21) Appl. No.: 15/845,702

(22) Filed: Dec. 18, 2017

(65) Prior Publication Data

US 2018/0106727 A1 Apr. 19, 2018

Related U.S. Application Data

(62) Division of application No. 14/006,317, filed as application No. PCT/JP2012/057422 on Mar. 23, 2012, now Pat. No. 9,851,309.

(30) Foreign Application Priority Data

Mar. 23, 2011 (JP) .................. 2011-063559

(51) Int. Cl.
| G01N 21/78 | (2006.01) |
| G01N 21/25 | (2006.01) |
| C12Q 1/00 | (2006.01) |
| C12Q 1/34 | (2006.01) |
| C12Q 1/42 | (2006.01) |
| C12Q 1/28 | (2006.01) |

(52) U.S. Cl.
CPC ............ *G01N 21/78* (2013.01); *C12Q 1/008* (2013.01); *C12Q 1/28* (2013.01); *C12Q 1/34* (2013.01); *C12Q 1/42* (2013.01); *G01N 21/25* (2013.01); *G01N 2333/90209* (2013.01); *G01N 2333/916* (2013.01); *G01N 2333/924* (2013.01)

(58) Field of Classification Search
CPC ............ C12Q 1/008; C12Q 1/28; C12Q 1/34; C12Q 1/42; G01N 21/25; G01N 21/78; G01N 2333/90209; G01N 2333/916; G01N 2333/924
See application file for complete search history.

(56) References Cited

U.S. PATENT DOCUMENTS

| 3,156,713 A | 11/1964 | Warnant et al. |
| 6,011,023 A | 1/2000 | Clark et al. |
| 2019/0106727 A1* | 4/2019 | Ito ........................... C12Q 1/68 |

FOREIGN PATENT DOCUMENTS

| JP | 2009-207396 A | 9/2009 |
| WO | 2008117816 A1 | 10/2008 |

OTHER PUBLICATIONS

Machine translation of WO 2008/117816, published Oct. 2, 2008.*
Porcelli, Adv. Immunol., Academic Press, 1995, vol. 59, p. 84.*
Extended Search Report for the related European Application No. 17197044.5, dated Feb. 6, 2018, 9 pages.
Anonymous, "Enzymatic Assay of PEROXIDASE, Product Information No. P-6782, Sigma", Oct. 4, 1996, pp. 1-4.
Iwai et al., "Highly Sensitive Activity Assay for β-galactosidaseUsing thio-NAD Cycling", Published by Graduate School of Pharmaceutical Sciences, Hokkaido University, Jan. 26, 2010, 4 pages.
Kishi et al., "Highly Sensitive Cholesterol Assay with Enzymatic Cycling Applied to Measurement of Remnant Lipoprotein-Cholesterol in Serum", Published in Clinical Chemistry 48:5, 2002, pp. 737-741.
Sprecher et al., "Steroid Phosphate Esters," Tetrahedron 55: 5465-5482 (1999), 18 pages.
Schneider, "Preparation and Properties of Some New Steroid β-D-Glucopyranosides, Steroid β-D-Glucopyranosiduric Acids, and Derivatives," Carbohyd. Res. 17: 199-207 (1971), 9 pages.
Hirotani et al., Biotransformation of Testosterone and Other Androgens by Suspension Cultures of Nicotiana tabacum "Bright Yellow," Phytochemistry 13: 2135-2142 (1974), 8 pages.
Skålhegg, 3α-Hydroxysteroid Dehydrogenase from Pseudomonas testosteroni: "Kinetic Properties with NAD and Its Thionicotinamide Analogue," Eur. J. Biochem. 50: 603-609 (1975), 7 pages.
Que et al., "Steroid Profiles Determined by Capillary Electrochromatography, Laser-Induced Fluorescence Detection and Electrospray-Mass Spectrometry," J. Chromatog. A 887: 379-391 (2000), 13 pages.
Forcellese et al., "D-Homo Steroids from Oxidation of 17-Methylene Steroids by Thallium(III) Nitrate," J. Org. Chem. 81: 3326-3328 (1981), 3 pages.
Pelecanou et al., "On the Synthesis of D-Homoandrostanes," Z. Naturforsch. 48b: 1305-1306 (1993), 2 pages.
Ertl, "Chemformatics Analysis of Organic Substituents: Identification of the Most Common Substituents, Calculation of Substituent Properties, and Automatic Identification of Drug-Like Bioisosteric Groups," J. Chem. Inf. Comput. Sci. 43: 374-380 (2003), 7 pages.
Ekins et al., "Human Pregnane X Receptor Antagonists and Agonists Define Molecular Requirements for Different Binding Sites," Mol. Pharmacol. 72: 592-603 (2007)., 12 pages.

(Continued)

*Primary Examiner* — Galina M. Yakovleva
(74) *Attorney, Agent, or Firm* — Ditthavong, Steiner & Mlotkowski

(57) ABSTRACT

Provided is a ultra-high-sensitivity assay in which the assay can be made on a commonly used assay apparatus such as an absorptiometer and a plate reader or with naked eyes. The high-sensitivity assay in which the assay can be made on a commonly used assay apparatus or with naked eyes can be provided by combining an enzyme cycling method using thio-NAD(P) as a coenzyme, a labeling enzyme and a substrate for the labeling enzyme optimally, and by amplifying thio-NAD(P)H, which is a signaling substance, exponentially and then quantifying the thio-NAD(P)H colorimetrically.

10 Claims, 22 Drawing Sheets

(56) References Cited

OTHER PUBLICATIONS

A web page, https://en.wikipedia.org/wiki/5%CE%B1-Androstane-3%CE%B2,17%CE%B2-diol, ("Wikipedia (5α-Androstane-3β,17β-diol"), 5 pages, retrieved Sep. 24, 2015.
A Partial Supplementary European Search Report on corresponding European Patent Application No. 12759947.0, issued by the European Patent Office dated Nov. 18, 2014, 11 pages.
An Office Action on corresponding European Patent Application No. 12759947.0, issued by the European Patent Office dated Mar. 6, 2015, 11 pages.
A Partial European Search Report in a corresponding European divisional patent application, European Divisional Patent Application Serial No. 15187872.5-1405, issued by the European Patent Office dated Jan. 22, 2016, 9 pages.
An Extended European Search Report and Search Opinion in a corresponding European divisional patent application, European Patent Application Serial No. 15187872.5-1405, issued by the European Patent Office dated May 17, 2016., 13 pages.
An International Search Report with Written Opinion of the International Searching Authority for corresponding International Application No. PCT/JP2012/057422, dated Jun. 19, 2012, 9 pages.
An International Preliminary Report on Patentability for corresponding International Application No. PCT/JP2012/057422, dated Sep. 26, 2013, 23 pages.
Japanese Office Action for corresponding JP Application No. 2012-533408, dated Oct. 30, 2012, 5 pages.
Japanese Office Action for corresponding JP Application No. 2011-063559, dated Jan. 24, 2012, 6 pages.

\* cited by examiner

ULTRA-HIGH-SENSITIVE ASSAY OF PROTEIN AND NUCLEIC ACID AND KIT, AND NOVEL ENZYME SUBSTRATE

CROSS-REFERENCES TO RELATED APPLICATIONS

The present application is a divisional application of U.S. patent application Ser. No. 14/006,317 by E. Ito, filed on Sep. 20, 2013, and entitled "Ultra-High-Sensitive Assay of Protein and Nucleic Acid and Kit, and Novel Enzyme Substrate," which in turn claimed the priority of Japanese Patent Application 2011-63559, filed on Mar. 23, 2011 by E. Ito and entitled "Ultra-High-Sensitive Assay of Protein and Nucleic Acid and Kit, and Novel Enzyme Substrate", and claimed the priority of PCT Patent Application PCT/JP2012/057422, filed on Mar. 23, 2012 by E. Ito and entitled "Ultra-High-Sensitive Assay of Protein and Nucleic Acid and Kit, and Novel Enzyme Substrate", the entire contents of all of these applications are hereby incorporated by reference.

FIELD OF THE INVENTION

The present invention relates to a high-sensitivity assay of protein and nucleic acid and a kit using an enzyme immunoassay and a nucleic acid probe assay. More particularly, the present invention relates to a method enabling ultra-high-sensitive assay of protein or nucleic acid while avoiding interference caused in thio-NAD cycling method used in these enzyme activity assay by employing an enzyme substrate specific to an enzyme labeled to an antibody or nucleic acid probe. The present invention further relates to novel enzyme substrates which can be used in the above high-sensitive assay of protein and nucleic acid and a kit.

BACKGROUND OF THE INVENTION

Although the radioimmunoassay (RIA) method is technically established as a high sensitivity measurement of protein or nucleic acid, under the present circumstances, it is impossible to change the aforementioned method to one having high sensitivity beyond $10^{-16}$ moles besides improvement of the sensitivity of a detection equipment. Additionally, by the RIA method, the place of measurement is not only limited to an isotope experimental facility, but the expiration date of reagents will become extremely short and the sensitivity of reagents will decrease rapidly. It also has the problem of radioactive waste problem to the method of radiation measurement. Especially the problem of abandonment in the case of using a long lasting nuclide is serious. Therefore, the research and development of the high sensitivity measurement of protein or nucleic acid has recently been developed using a non-radioactive alternative. Thus most of the research and development and the technical improvement about the RIA method is not performed in the actual conditions.

A high sensitivity measurement replaced with the RIA method, which is enzyme immunoassay (ELISA method) in the measurement of protein (FIG. 1), and PCR method in the measurement of nucleic acid. The enzyme immunoassay can be proceed to high sensitivity ($10^{-15}$ moles) by the fluorescence method and the emitting light method from sensitivity of $10^{-13}$ moles by the colorimetric assay in the initial development, and the development and improvement of the exclusive measurement device are also proceeding. How- ever, the sensitivity has been arrived to limit, just the operation of measurement is simple.

Moreover, in the PCR method of the high sensitivity measurement of nucleic acid, there is a problem of the detection of specific signal for target molecule, the amplification efficiency and the condition of PCR product arriving at a plateau; the quantification of nucleic acid is difficult strictly.

The enzyme immunoassay using antibody-enzyme complex and the nucleic acid probe assay using a nucleic acid-enzyme complex using thio-NAD cycling assay is already known. (Refer to WO2008/117816 (Patent document 1)).

SUMMARY OF THE INVENTION

Problems to be Solved by the Invention

According to the method of Patent document 1, the enzyme immunoassay was combined with the enzymatic cycling method which uses as a substrate producing by the labeling enzyme using the enzyme immunoassay, and thio-NAD(P)H as a signal substance is amplified geometric-progressive, and by a calorimetric assay method, it results in the quantification of protein or nucleic acid and the detection by nucleic acid. However it revealed that not necessarily high reactivity of the labeled enzyme and substrate, and the substrate of labeled cycling enzyme partially inhibits the enzyme reaction in the enzymatic cycling reaction.

The object of the present invention is in the enzyme immunoassay, the method being combined with the cycling method which uses as a substrate produced by the labeled enzyme used in enzyme immunoassay, solving the aforementioned problem of the substrate to labeled enzyme, and using a colorimetric assay method, high sensitivity detection method of protein or nucleic acid by colorimetric assay of the easiest method, and providing the assay of increasing the sensitivity to geometric-progressive degree. In particular, an assay method is provided which raises sensitivity to more than $10^{-18}$ moles.

The present inventor has succeeded in obtaining a compound as a substrate to labeled enzyme solving the aforementioned problem or providing the new compound, and therefore using these substrates, he has succeeded in solving the aforementioned problem, thus the present invention has been completed.

Means for Solving the Problems

The present invention is as follows:

[1] A method of assaying enzyme activity using an antibody-enzyme complex, wherein alkaline phosphatase, glucosidase, galactosidase, fructosidase, mannosidase or peroxidase is used as an enzyme of the antibody-enzyme complex, and an androsterone derivative represented by the following formula (1) is used as a substrate of the enzyme,

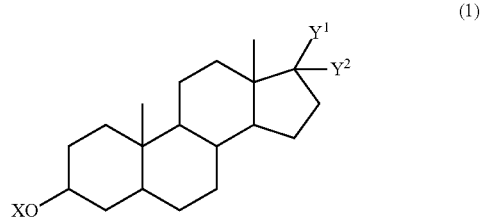

wherein:

(i) X represents a phosphate group, and $Y^1$ and $Y^2$ represent together a methylene group, or $Y^1$ represents hydrogen, and $Y^2$ represents hydrogen, a hydroxyl group, a $C_{1-6}$ alkoxy group, or a $C_{1-6}$ alkyl group when the androsterone derivative represented by the formula (1) is used as a substrate of alkaline phosphatase, (ii) X represents a sugar moiety, the sugar moiety represents one selected from the group consisting of glucose, galactose, fructose and mannose, and $Y^1$ and $Y^2$ represent together a methylene group or an oxygen atom, or $Y^1$ represents hydrogen, and $Y^2$ represents hydrogen, a hydroxyl group, a $C_{1-6}$ alkoxy group, or a $C_{1-6}$ alkyl group when the androsterone derivative represented by the formula (1) is used as a substrate of glucosidase, galactosidase, fructosidase or mannosidase, or (iii) X represents —O—CO—R (provided that R represents a $C_{1-6}$ alkyl group or a phenyl group), $Y^1$ and $Y^2$ represent together a methylene group or an oxygen atom, or $Y^1$ represents hydrogen, and $Y^2$ represents hydrogen, a hydroxyl group, a $C_{1-6}$ alkoxy group, or a $C_{1-6}$ alkyl group when the androsterone derivative represented by the formula (1) is used as a substrate of peroxidase, and a quantification of a product of the enzyme reaction is performed by producing thio-NADH and/or thio-NADPH by enzyme cycling reaction using NADH and/or NADPH, thio-NAD and/or thio-NADP, and hydroxysteroid dehydrogenase (HSD), and assaying the amount of the produced thio-NADH and/or thio-NADPH, or measuring the change of the color by the produced thio-NADH and/or thio-NADPH.

[2] A method of assaying a nucleic acid probe using an enzyme-labeled nucleic acid probe, wherein alkaline phosphatase, glucosidase, galactosidase, fructosidase, mannosidase or peroxidase is used as an enzyme of the enzyme-labeled nucleic acid probe, and an androsterone derivative represented by the following formula (1) is used as a substrate of the enzyme,

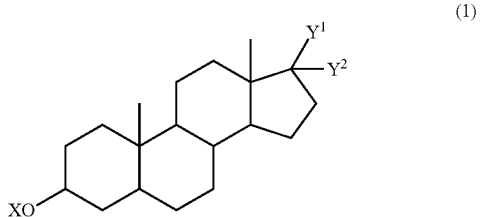

(1)

wherein (i) X represents a phosphate group, and $Y^1$ and $Y^2$ represent together a methylene group, or $Y^1$ represents hydrogen, and $Y^2$ represents hydrogen, a hydroxyl group, a $C_{1-6}$ alkoxy group, or a $C_{1-6}$ alkyl group when the androsterone derivative represented by the-formula (1) is used as a substrate of alkaline phosphatase, (ii) X represents a sugar moiety, the sugar moiety represents one selected from the group consisting of glucose, galactose, fructose and mannose, and $Y^1$ and $Y^2$ represent together a methylene group or an oxygen atom, or $Y^1$ represents hydrogen, and $Y^2$ represents hydrogen, a hydroxyl group, a $C1_6$ alkoxy group, or a $C1.6$ alkyl group when the androsterone derivative represented by the formula (1) is used as a substrate of glucosidase, galactosidase, fructosidase or mannosidase, or (iii) X represents —O—CO—R (provided that R represents a C1_6 alkyl group or a phenyl group), $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group when the androsterone derivative represented by the formula (1) is used as a substrate of peroxidase, and a quantification of a reaction product of the enzyme reaction is performed by producing thio-NADH and/or thio-NADPH by enzyme cycling reaction using NADH and/or NADPH, thio-NAD and/or thio-NADP, and hydroxysteroid dehydrogenase (HSD), and assaying the amount of the produced thio-NADH and/or thio-NADPH, or measuring the change of the color by the produced thio-NADH and/or thio-NADPH.

[3] The method according to [1] or [2], wherein the enzyme is alkaline phosphatase, and X represents a phosphate group, $Y^1$ and $Y^2$ represent together a methylene group, or $Y^1$ represents hydrogen, and $Y^2$ represents hydrogen, a hydroxyl group, a $C_1$-$C_6$ alkoxy group, or a $C_1$-$C_6$ alkyl group in the androsterone derivative represented by the formula (1).

[4] The method according to [1] or [2], wherein the enzyme is glucosidase, galactosidase, fructosidase or mannosidase, and X represents a sugar moiety, the sugar moiety represents one selected from the group consisting of glucose, galactose, fructose and mannose, and $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group in the androsterone derivative represented by the formula (1).

[5] The method according to [1] or [2], wherein the enzyme is peroxidase, and

X represents —O—CO—R (provided that R represents a $C_1$-$C_6$ alkyl group or a phenyl group), and $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group in the androsterone derivative represented by the formula (1).

[6] A kit for enzyme immunoassay comprising reagents (1) to (5) described below:

(1) alkaline phosphatase labeled with an antibody specific to a target protein antigen, (2) an androsterone derivative represented by the formula (1), which is a substrate of the enzyme described above

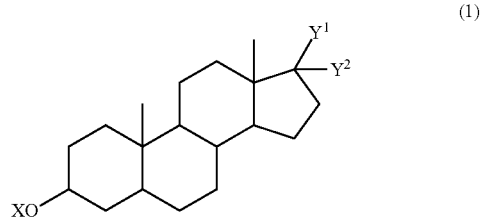

(1)

(wherein, X represents a phosphate group, $Y^1$ and $Y^2$ represent together a methylene group, or $Y^1$ represents hydrogen, and $Y^2$ represents hydrogen, a hydroxyl group, a $C_1$-$C_6$ alkoxy group, or a $C_1$-$C_6$ alkyl group), (3) hydroxysteroid dehydrogenase (HSD), (4) NADH and/or NADPH, and (5) thio-NAD and/or thio-NADP.

[7] A kit for enzyme immunoassay comprising reagents (1) to (5) below:
(1) glucosidase, galactosidase, fructosidase or mannosidase which is labeled with an antibody specific to a target protein antigen,
(2) an androsterone derivative represented by the formula (1), which is a substrate of the enzyme described above

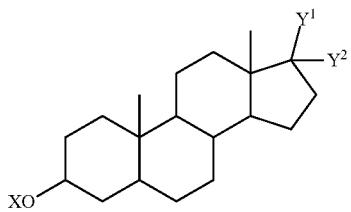

(wherein X represents a sugar moiety, the sugar moiety represents one selected from the group consisting of glucose, galactose, fructose and mannose, and $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group),
(3) hydroxysteroid dehydrogenase (HSD)
(4) NADH and/or NADPH, and
(5) thio-NAD and/or thio-NADP.

[8] A kit for enzyme immunoassay comprising reagents (1) to (5) below:
(1) peroxidase labeled with an antibody specific to a target protein antigen,
(2) an androsterone derivative represented by the formula (1), which is a substrate of the enzyme described above

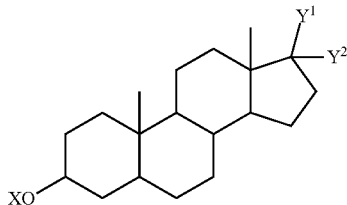

(3) hydroxysteroid dehydrogenase (HSD),
(4) NADH and/or NADPH, and
(5) thio-NAD and/or thio-NADP.

[9] A kit for assaying a nucleic acid probe comprising reagents (1) to (5) below:
(1) alkaline phosphatase labeled with a nucleic acid probe specifically binding to a target nucleic acid,
(2) an androsterone derivative represented by the formula (1), which is a substrate of the enzyme described above

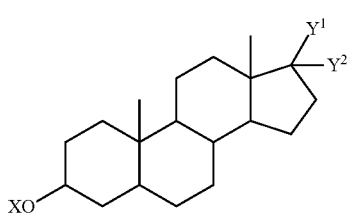

(wherein X represents a phosphate group, $Y^1$ and $Y^2$ represent together a methylene group, or $Y^1$ represents hydrogen, and $Y^2$ represents hydrogen, a hydroxyl group, a $C_1$-$C_6$ alkoxy group, or a $C_1$-$C_6$ alkyl group),
(3) hydroxysteroid dehydrogenase (HSD),
(4) NADH and/or NADPH, and
(5) thio-NAD and/or thio-NADP.

[10] A kit for assaying a nucleic acid probe comprising reagents (1) to (5) below:
(1) glucosidase, galactosidase, fructosidase or mannosidase labeled with a nucleic acid probe specifically binding to a target nucleic acid,
(2) an androsterone derivative represented by the formula (1), which is a substrate of the enzyme described above

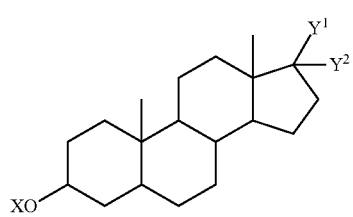

(wherein X represents a sugar moiety, the sugar moiety represents one selected from the group consisting of glucose, galactose, fructose and mannose, and $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group),
(3) hydroxysteroid dehydrogenase (HSD),
(4) NADH and/or NADPH, and
(5) thio-NAD and/or thio-NADP.

[11] A kit for assaying a nucleic acid probe comprising reagents (1) to (5) below:
(1) peroxidase labeled with a nucleic acid probe specifically binding to a target nucleic acid,
(2) an androsterone derivative represented by the formula (1), which is a substrate of the enzyme described above

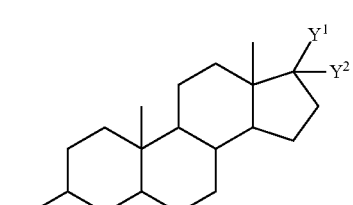

(wherein X represents —O—CO—R (provided that R represents a $C_1$-$C_6$ alkyl group or a phenyl group), $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group),
(3) hydroxysteroid dehydrogenase (HSD),
(4) NADH and/or NADPH, and
(5) thio-NAD and/or thio-NADP.

[12] An androsterone derivative represented by the formula (1) below:

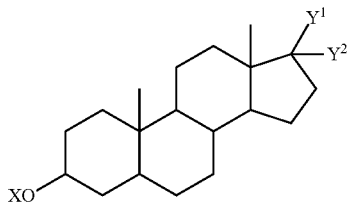

(wherein, definitions of X, Y$^1$ and Y$^2$ are those of any one of (A), (B) and (C) below):

(A) X represents a phosphate group, Y$^1$ and Y$^2$ represent together a methylene group, or Y$^1$ represents hydrogen, and Y$^2$ represents a hydroxyl group, a $C_1$-$C_6$ alkoxy group or a $C_1$-$C_6$ alkyl group, (B) X represents one of a sugar moiety selected from the group consisting of glucose, galactose, fructose and mannose, Y$^1$ and Y$^2$ represent together a methylene group, or Y$^1$ represents hydrogen, and Y$^2$ represents hydrogen, a $C_1$-$C_6$ alkoxy group, or a $C_1$-$C_6$ alkyl group, (C) X represents —O—CO—R, R represents a C1.6 alkyl group or a phenyl group, and Y$^1$ and Y$^2$ represent together a methylene group or an oxygen atom, or Y$^1$ represents hydrogen, and Y$^2$ represents hydrogen, a hydroxyl group, a $C_1$-$C_6$ alkoxy group, or a $C_1$-$C_6$ alkyl group).

[13] The androsterone derivative according to [12] wherein the definitions of X, Y$^1$ and Y$^2$ are those of (A), X represents a phosphate group, and Y$^1$ and Y$^2$ represent together a methylene group, or Y$^1$ represents hydrogen, and Y$^2$ represents a hydroxyl group, a $C_1$-$C_6$ alkoxy group or a $C_1$-$C_6$ alkyl group.

[14] The androsterone derivative according to [12] wherein the definitions of X, Y$^1$ and Y$^2$ are those of (B), X represents one of a sugar moiety selected from the group consisting of glucose, galactose, fructose and mannose, and Y$^1$ and Y$^2$ represent together a methylene group, or Y$^1$ represents hydrogen, and Y$^2$ represents hydrogen, a C1_6 alkoxy group, or a C1-6 alkyl group.

[15] The androsterone derivative according to [12] wherein the definitions of X, Y$^1$ and Y$^2$ are those of (C), X represents —O—CO—R, R represents a $C_1$-$C_6$ alkyl group or a phenyl group, and Y$^1$ and Y$^2$ represent together a methylene group or an oxygen atom, or Y$^1$ represents hydrogen, and Y$^2$ represents hydrogen, a hydroxyl group, a $C_1$-$C_6$ alkoxy group, or a $C_1$-$C_6$ alkyl group.

Effects of the Invention

According to the present invention, it is possible to provide an enzyme immunoassay enhancing the assay sensitivity to $10^{-18}$ moles or more, and to measure a target protein or target nucleic acid in high sensitivity.

BEST MODE FOR CARRYING OUT THE INVENTION

Figure 1:
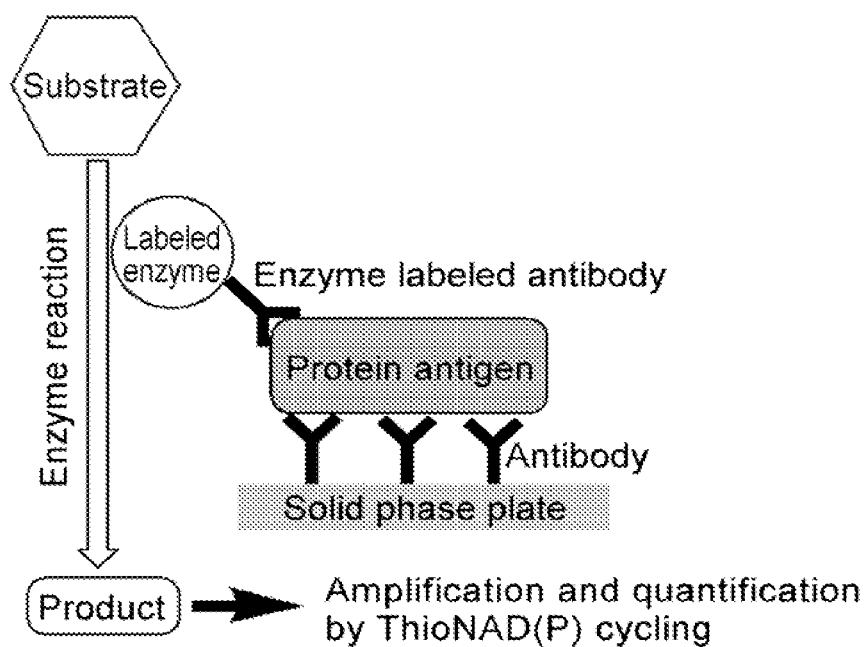
FIG. 1 is the assay principle of the enzyme immunoassay (ELISA method)

[Novel substrate] The present invention relates to an androsterone derivative represented by the following formula (1):

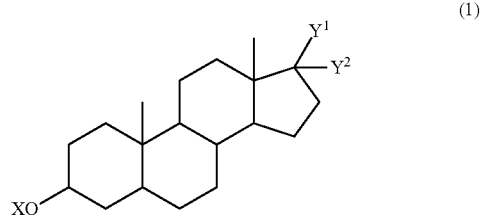

(wherein, definitions of X, Y$^1$ and Y$^2$ are those of any one of (A), (B) and (C) described below).

(A) X represents a phosphate group, and Y$^1$ and Y$^2$ represent together a methylene group, or Y$^1$ represents hydrogen, and Y$^2$ represents a hydroxyl group, a $C_1$-$C_6$ alkoxy group or a $C_1$-$C_6$ alkyl group, (B) X represents one kind of a sugar moiety selected from a group consisting of glucose, galactose, fructose and mannose, Y$^1$ and Y$^2$ represent together a methylene group, or Y$^1$ represents hydrogen, and Y$^2$ represents hydrogen, a $C_1$-$C_6$ alkoxy group, or a $C_1$-$C_6$ alkyl group, (C) X represents —O—CO—R, R represents a $C_1$-$C_6$ alkyl group or a phenyl group, and Y$^1$ and Y$^2$ represent together a methylene group or an oxygen atom, or Y$^1$ represents hydrogen, and Y$^2$ represents hydrogen, a hydroxyl group, a $C_1$-$C_6$ alkoxy group, or a $C_1$-$C_6$ alkyl group.)

The $C_1$-$C_6$ alkoxy group as an example of Y$^2$ may be, for example, a methoxy group, an ethoxy group, a propoxy group and the like, and the $C_1$-$C_6$ alkyl group may be, for example, a methyl group, an ethyl group, an iso-propyl group, an n-propyl group, a tert-butyl group, an n-butyl group, an n-pentyl group, an n-hexyl group and the like.

The sugar of the sugar moiety can be comprised of glucose, galactose, fructose or mannose, and can be suitably selected depending on a labeling enzyme to be used.

—CO— in —O—CO—R means —(C=O)—, and the $C_1$-$C_6$ alkyl group in R may be, for example, a methyl group, an ethyl group, an iso-propyl group, an n-propyl group, a tert-butyl group, an n-butyl group, an n-pentyl group, an n-hexyl group and the like. In addition, R may be a phenyl group, and may have a functional group.

When $Y^1$ and $Y^2$ represent together an oxygen atom, X represents a sugar moiety or —O—CO—R, specifically a sugar derivative of 5α-androsterone or 5β-androsterone, for example, glucoside, galactoside, fructoside or mannoside. Meanwhile, glucoside, galactoside, fructoside and mannoside are formally referred to as glucopyranoside, galactopyranoside, fructopyranoside and mannopyranoside, respectively.

Specific examples of the compound of the present invention are listed in Table 1 to be described below. However, Table 1 includes compounds that can be used in the method and the kit of the present invention besides the specific examples of the compound of the present invention.

These compounds of the present invention can be synthesized based on or in reference to the methods described in Examples.

[Enzyme cycling assay] The present invention relates to an enzyme assay using an antibody-enzyme complex, in which a quantification of a reaction product by the enzyme of the antibody-enzyme complex is performed by producing thio-NADH and/or thio-NADPH by enzyme cycling reaction using NADH and/or NADPH, thio-NAD and/or thio-NADP, and dehydrogenase (DH), and assaying the amount of the produced thio-NADH and/or thio-NADPH, or measuring the change of the color by the produced thio-NADH and/or thio-NADPH.

The antibody-enzyme complex consists of an antibody specific to a target protein antigen and an enzyme labeled with this antibody, and is used in the assay of the above-mentioned target protein.

Furthermore, the present invention relates to a method of assaying a nucleic acid probe using an enzyme-labeled nucleic acid probe, in which a quantification of a reaction product by the enzyme of the enzyme-labeled nucleic acid probe is performed producing thio-NADH and/or thio-NADPH by enzymatic cycling reaction using NADH and/or NADPH, thio-NAD and/or thio-NADP, and dehydrogenase (DH), and assaying the amount of the produced thio-NADH and/or thio-NADPH, or measuring the change of the color by the produced thio-NADH and/or thio-NADPH.

The enzyme-labeled nucleic acid probe consists of a nucleic acid probe specifically binding to a target nucleic acid and an enzyme labeled with this nucleic acid probe, and is used in the assay of the above-mentioned target nucleic acid.

In the method of the present invention, the enzyme (labeling enzyme) of the antibody-enzyme complex or the enzyme-labeled nucleic acid probe used is alkaline phosphatase (ALP), galactosidase, glucosidase, fructosidase, mannosidase or peroxidase. As a substrate of the above enzyme, the androsterone derivative represented by the following formula (1) is used.

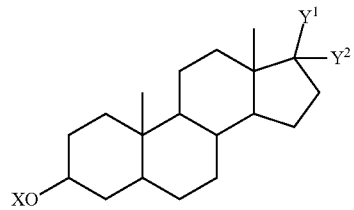

(1)

(i) In the case where the androsterone derivative represented by the formula (1) is used as a substrate of alkaline phosphatase, X represents a phosphate group, $Y^1$ and $Y^2$ represent together a methylene group, or $Y^1$ represents hydrogen, and $Y^2$ represents hydrogen, a hydroxyl group, a $C_1$-$C_6$ alkoxy group, or a $C_1$-$C_6$ alkyl group. The androsterone derivative encompassed in the case of (i) further includes compounds wherein $Y^2$ is hydrogen as well as the novel compounds of the present invention. The compound in which $Y^2$ is hydrogen is described in Tetrahedron, 1999, Vol. 55, No. 17, p. 5465-5482. The entire contents of the description of this literature are hereby incorporated by reference.

(ii) In the case where the androsterone derivative represented by the formula (1) is used as a substrate of galactosidase, glucosidase, fructosidase or mannosidase, X represents a sugar moiety, the sugar moiety represents one kind selected from the group consisting of glucose, galactose, fructose and mannose, and $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group. The androsterone derivative encompassed in the case of (ii) further includes compounds in which $Y^1$ and $Y^2$ represent together an oxygen atom as well as the novel compounds of the present invention. A compound in which X represents glucose when $Y^1$ and $Y^2$ represent together an oxygen atom, is described in Carbohydrate Research, 1971, Vol. 17, No. 1, p. 199-207. The entire contents of the description of this literature are hereby incorporated by reference. A compound in which X represents glucose when $Y^2$ represents a hydroxyl group, is described in Phytochemistry, 1974, Vol. 13, No. 10, p. 2135-2142. The entire contents of the description of this literature are hereby incorporated by reference.

(iii) In the case where the androsterone derivative represented by the formula (1) is used as a substrate of peroxidase, X represents —O—CO—R (provided that R represents a $C_1$-$C_6$ alkyl group or a phenyl group), $Y^1$ and $Y^2$ represent together a methylene group or an oxygen atom, or $Y^1$ represents hydrogen, and $Y^2$ represents hydrogen, a hydroxyl group, a $C_1$-$C_6$ alkoxy group, or a $C_1$-$C_6$ alkyl group. The androsterone derivative encompassed in the case of (iii) is the novel compound of the present invention.

The ultra-high sensitivity assay of the present invention can be carried out similarly to an ordinary enzyme immunoassay or nucleic acid probe assay. For example, a solid phase carrier may be used, which is used in an ordinary assay, for example, a solid phase carrier such as a microplate or plastic tube, a magnetic bead and the like in which an antibody or nucleic acid probe specifically binding to a subject is immobilized on the surface.

The antibody and the nucleic acid probe-enzyme complex can be prepared by an ordinary method.

The antibody constituting the antibody-enzyme complex can be suitably selected from the antibodies that specifically bind to a subject to be measured by the enzyme immunoassay of the present invention. For example, the enzyme immunoassay of the present invention is used in an assay of a protein, and herein the antibody consisting of the antibody-enzyme complex is an antibody specifically binding to a protein which is the subject. In addition, in this case, a basal plate is used in which an antibody specifically binding to the subject protein is immobilized on the surface. In addition, the antibody constituting the antibody-enzyme complex and the antibody immobilized on the basal plate can be a fragment of the antibody. In the present invention of the enzyme immunoassay, the subject is not limited to a protein, and can be any substance that is a measuring subject of an ordinary enzyme immunoassay besides a protein.

In the nucleic acid probe enzyme complex, the probe can be suitably selected similarly from the probes complementary to a nucleic acid probe that is complementary to a measuring subject.

In the method of the present invention, the quantification of a reaction product by the enzyme of the antibody-enzyme complex or the enzyme of the enzyme-labeled nucleic acid probe is performed by producing thio-NADH and/or thio-NADPH by enzymatic cycling reaction using NADH and/or NADPH, thio-NAD and/or thio-NADP, and dehydrogenase (DH), and assaying the amount of the produced thio-NADH and/or thio-NADPH, or measuring the change of the color by the produced thio-NADH and/or thio-NADPH.

In the method of the present invention, the concentration of each component can be in the range to be described below.

(1) Concentration range of the antibody-enzyme complex or the enzyme-labeled nucleic acid probe: 0.01 pg/mL to 1 mg/mL;

(2) Concentration range of the substrate of the labeling enzyme: 1 pM to 500 mM;

(3) Concentration range of the NADH and/or NADPH: 0.01 mM to 50 mM;

(4) Concentration range of the thio-NAD and/or thio-NADP: 0.01 mM to 100 mM; and (5) Concentration range of the dehydrogenase (DH): 0.01 U/mL to 5000 U/mL.

The reaction conditions can be suitably determined by considering the optimum temperature range of the labeling enzyme and the dehydrogenase (DH). For example, as for the reaction temperature, the reaction is preferably carried out at room temperature from a point of simple manipulation. However, the reaction can be carried out at higher temperature or lower temperature than room temperature by considering the optimum temperature range of the labeling enzyme and the dehydrogenase (DH).

The reaction time can be a time sufficient for accumulating thio-NADH and/or thio-NADPH, so as to enable the assay of the amount of the produced thio-NADH and/or thio-NADPH, or the measurement of the change of the color by the produced thio-NADH and/or thio-NADPH. However, the accumulation amount of thio-NADH and/or thio-NADPH necessary for the assay or measurement varies depending on the conditions of the assay or measurement, and can be suitably determined depending on the conditions.

The cycling system using thio-NAD(P) in the enzymatic cycling system is a unique cycling system that appeared relatively recently. With this system, the cycling is performed that is, thio-NAD(P)/thio-NAD(P)H using dehydrogenase (DH) with NAD(P)/NAD(P)H as a co-enzyme under conditions of coexistence of NAD(P)/NAD(P)H and its analog, and the amplification and the quantification are performed with thio-NAD(P)H (maximum absorption wavelength: 400 nm, molar absorption coefficient=11,900) as a substrate of dehydrogenase. The principle for measurement of the thio-NAD(P)cycling system is as described below.

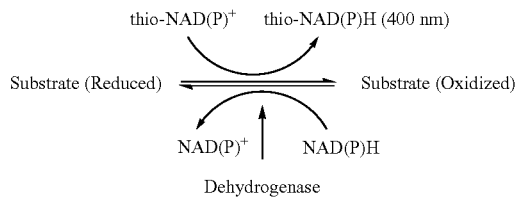

Dehydrogenase

Whereas the NADH exhibits the maximum absorption at 340 nm (molar absorption coefficient=6,200), thio-NAD(P)H exhibits absorption in the visible range (maximum absorption wavelength: 400 nm, molar absorption coefficient=11,900) and thus the thio-NAD(P)cycling method has an advantage of enabling measurement using a popular absorption spectrophotometer or a microplate reader for colorimetric measurement.

Using the advantages that measurement in the cycling system using thio-NAD(P) can be performed by using a popular absorption spectrophotometer or a microplate reader for colorimetric measurement, some conventional methods based on the increase of NADH absorption, such as an assay of dehydrogenase activity and quantification of a substrate thereof, have been improved to a method using thio-NAD. However, there has been no report yet for use of this cycling system in sensitivity improvement as a detection system such as an enzyme immunoassay. In the present invention, the combination of a labeling enzyme and the cycling system enables the amplification reaction to be exponential reaction for the first time, whereby resulting in sufficient sensitivity improvement.

According to the assay of the present invention, as it is exemplified in the enzyme immunoassay, the products produced with the enzyme complex and a substrate in combination are used as the substrate of the next enzymatic cycling reaction, and the absorption of thio-NAD(P)H produced by the enzymatic cycling reaction is quantified colorimetrically. The enzymatic cycling is performed with a dehydrogenase in this reaction, and thus either a reduced substrate or an oxidized substrate can be used as a substrate of the enzymatic cycling reaction.

In the present invention, the labeling enzyme used as the enzyme complex, the substrate thereof and the dehydrogenase subsequently used in the cycling reaction have the properties as described below:

(1) The product of the labeling enzyme is androsterone or a derivative thereof;

(2) Commercially available and widely used labeling enzymes can be used;

(3) The turnover number of the enzymatic cycling is great; and (4) Dehydrogenase used in this cycling reaction has no contamination of the labeling enzyme or similar activity to that of the labeling enzyme.

Examples of the dehydrogenase (DH) may include, for example, 3α-hydroxysteroid dehydrogenase.

Examples of a representative combination of the labeling enzyme, the substrate and the dehydrogenase for the enzyme cycling that can be used in the present invention will be described below. However, of course, the combination is not limited to these combinations.

TABLE 1

| Labeled Enzyme | Substrate | Dehydrogenase |
|---|---|---|
| α-glucosidase | 5α-androsterone 3α-glucoside | 3α-hydroxysteroid dehydrogenase |
| α-glucosidase | 5β-androsterone 3α-glucoside | 3α-hydroxysteroid dehydrogenase |
| α-glucosidase | 3α-hydroxy-17β-methoxy-5α-androstane 3-α-glucoside | 3α-hydroxysteroid dehydrogenase |
| α-glucosidase | 3α-hydroxy-17β-methoxy-5β-androstane 3-α-glucoside | 3α-hydroxysteroid dehydrogenase |
| β-glucosidase | 5α-androsterone 3-β-glucoside | 3α-hydroxysteroid dehydrogenase |
| β-glucosidase | 5β-androsterone 3-β-glucoside | 3α-hydroxysteroid dehydrogenase |
| β-glucosidase | 3α-hydroxy-17β-methoxy-5α-androstane 3-β-glucoside | 3α-hydroxysteroid dehydrogenase |
| β-glucosidase | 3α-hydroxy-17β-methoxy-5β-androstane 3-β-glucoside | 3α-hydroxysteroid dehydrogenase |
| β-galactosidase | 5α-androsterone 3-β-galactoside | 3α-hydroxysteroid dehydrogenase |
| β-galactosidase | 5β-androsterone 3-β-galactoside | 3α-hydroxysteroid dehydrogenase |
| β-galactosidase | 3α-hydroxy-17β-methoxy-5α-androstane 3-β-galactoside | 3α-hydroxysteroid dehydrogenase |
| β-galactosidase | 3α-hydroxy-17β-methoxy-5β-androstane 3-β-galactoside | 3α-hydroxysteroid dehydrogenase |
| Acid phosphatase | 3α-hydroxy-17β-methyl-5α-androstane 3-phosphate | 3α-hydroxysteroid dehydrogenase |
| Acid phosphatase | 3α-hydroxy-17β-methyl-5β-androstane 3-phosphate | 3α-hydroxysteroid dehydrogenase |
| Acid phosphatase | 3α-hydroxy-17β-methoxy-5α-androstane 3-phosphate | 3α-hydroxysteroid dehydrogenase |
| Acid phosphatase | 3α-hydroxy-17β-methoxy-5β-androstane 3-phosphate | 3α-hydroxysteroid dehydrogenase |
| Acid phosphatase | 3α,17α-dihydroxy-17β-methyl-5α-androstane 3-phosphate | 3α-hydroxysteroid dehydrogenase |
| Acid phosphatase | 3α,17α-dihydroxy-17β-methyl-5β-androstane 3-phosphate | 3α-hydroxysteroid dehydrogenase |
| Acid phosphatase | 3α,17α-dihydroxy-17β-ethyl-5α-androstane 3-phosphate | 3α-hydroxysteroid dehydrogenase |
| Acid phosphatase | 3α,17α-dihydroxy-17β-ethyl-5β-androstane 3-phosphate | 3α-hydroxysteroid dehydrogenase |
| Acid phosphatase | 17β-acetoxy-3α-hydroxy-5α-androstane 3-phosphate | 3α-hydroxysteroid dehydrogenase |
| Acid phosphatase | 17β-acetoxy-3α-hydroxy-5β-androstane 3-phosphate | 3α-hydroxysteroid dehydrogenase |
| Alkaline phosphatase | 3α-hydroxy-17β-methyl-5α-androstane 3-phosphate | 3α-hydroxysteroid dehydrogenase |
| Alkaline phosphatase | 3α-hydroxy-17β-methyl-5β-androstane 3-phosphate | 3α-hydroxysteroid dehydrogenase |
| Alkaline phosphatase | 3α-hydroxy-17β-methoxy-5α-androstane 3-phosphate | 3α-hydroxysteroid dehydrogenase |
| Alkaline phosphatase | 3α-hydroxy-17β-methoxy-5β-androstane 3-phosphate | 3α-hydroxysteroid dehydrogenase |
| Alkaline phosphatase | 3α,17α-dihydroxy-17β-methyl-5α-androstane 3-phosphate | 3α-hydroxysteroid dehydrogenase |
| Alkaline phosphatase | 3α,17α-dihydroxy-17β-methyl-5β-androstane 3-phosphate | 3α-hydroxysteroid dehydrogenase |
| Alkaline phosphatase | 3α,17α-dihydroxy-17β-ethyl-5α-androstane 3-phosphate | 3α-hydroxysteroid dehydrogenase |
| Alkaline phosphatase | 3α,17α-dihydroxy-17β-ethyl-5β-androstane 3-phosphate | 3α-hydroxysteroid dehydrogenase |
| Alkaline phosphatase | 5β-androstane 3-phosphate | 3α-hydroxysteroid dehydrogenase |
| Alkaline phosphatase | 17β-acetoxy3α-hydroxy-5α-androstane 3-phosphate | 3α-hydroxysteroid dehydrogenase |
| Alkaline phosphatase | 17β-acetoxy3α-hydroxy-5β-androstane 3-phosphate | 3α-hydroxysteroid dehydrogenase |
| Sulfatase | 5α-androstane 3-sulfate | 3α-hydroxysteroid dehydrogenase |
| Sulfatase | 5β-androstane 3-sulfate | 3α-hydroxysteroid dehydrogenase |
| Peroxidase | 3α-tert-butyl-peroxy-5α-androstane | 3α-hydroxysteroid dehydrogenase |
| Peroxidase | 3α-tert-butyl-peroxy-5β-androstane | 3α-hydroxysteroid dehydrogenase |
| Peroxidase | 3α-benzoyl-peroxy-5α-androstane | 3α-hydroxysteroid dehydrogenase |
| Peroxidase | 3α-benzoyl-peroxy-5β-androstane | 3α-hydroxysteroid dehydrogenase |

TABLE 1-continued

| Labeled Enzyme | Substrate | Dehydrogenase |
|---|---|---|
| Peroxidase | 3α-acetyl-peroxy-5α-androstane | 3α-hydroxysteroid dehydrogenase |
| Peroxidase | 3α-acetyl-peroxy-5β-androstane | 3α-hydroxysteroid dehydrogenase |

For example, when 3α-hydroxysteroid dehydrogenase is used as the cycling enzyme among the combinations described above, examples of a candidate for the substrate that can be used include androsterone, 11β-hydroxyandrosterone, 11-oxoandrosterone and 11α-hydroxyandrosterone.

The substrate for the cycling is preferably those having fast enzyme reaction rate (having high activity for the In addition, similarly, peroxidase, which is widely used as a labeling enzyme, and peroxide of an androsterone derivative, for example, tert-butyl peroxide are also a preferable combination in a point of easy synthesis.

A reaction example using androsterone 3-β-D galactoside as a substrate will be described below.

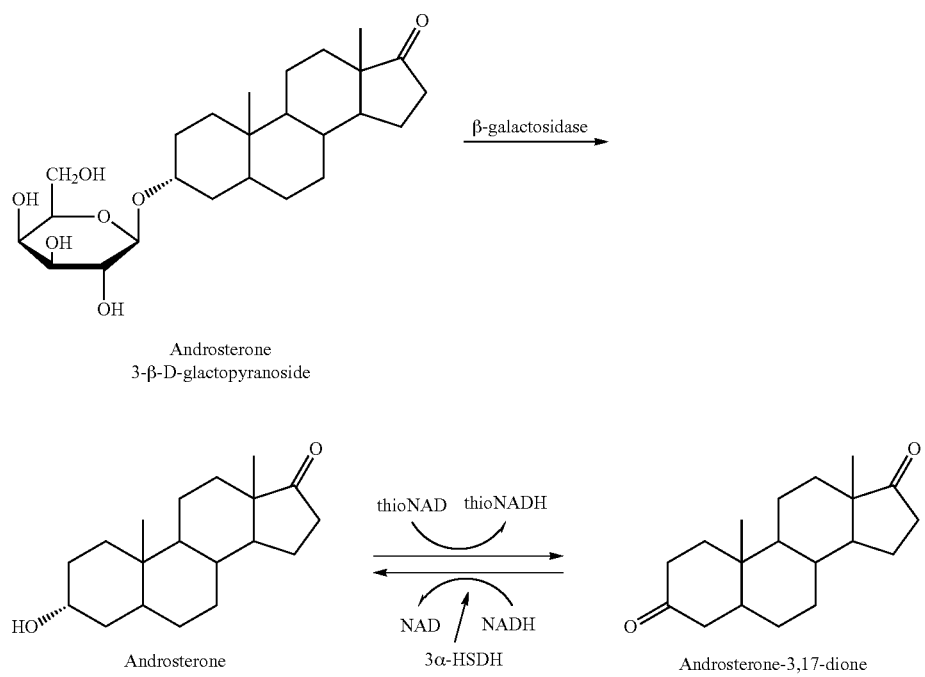

substrate) and reacting even at a low concentration (having low $K_m$ value). In addition, a desirable property as the dehydrogenase is the reaction rate when using thio-NAD(P) as a co-enzyme. In the dehydrogenation reaction of androsterone by other many dehydrogenases, the reaction rate when thio-NAD is used as a co-enzyme is within several % of the reaction rate when NAD is used, while with 3α-hydroxysteroid dehydrogenase, the reaction rate with thio-NAD is about 59% of the reaction rate with NAD. Thus, 3α-hydroxysteroid dehydrogenase has a desirable property as the cycling enzyme of the present invention. Furthermore, widely used alkaline phosphatase (ALP) can be used as the labeling enzyme to be combined, and the combination with alkaline phosphatase is preferable also in a point of easy synthesis of a phosphate ester of an androsterone derivative at the position 3 that is a substrate of alkaline phosphatase.

In addition, similarly, glucosidase, which is widely used as a labeling enzyme, and glucoside of an androsterone derivative, and galactosidase and galactoside of an androsterone derivative are a preferable combination in a point of easy synthesis.

An enzyme immunoassay using alkaline phosphatase (ALP) as the enzyme of the antibody-enzyme complex will be explained below as an example. Alkaline phosphatase (ALP) is an enzyme widely used as a labeling enzyme, and when the androsterone derivative, the novel compound is used as a substrate of ALP in an enzyme immunoassay using this ALP, androsterone is produced as a reaction product. Then, 3α-hydroxysteroid dehydrogenase (3α-HSD), which dehydrogenase uses the reaction product of ALP as a substrate, is used in the enzyme cycling reaction.

The thio-NAD cycling enables the amplification and the quantification of the substrate of dehydrogenase in an efficiency of hundreds of cycles per minute if an appropriate dehydrogenase reaction is selected. Consequently, the activity of the enzyme presenting such a substrate as the reaction product can be assayed by the thio-NAD cycling in ultra-high sensitivity.

[Kit for enzyme cycling] The present invention encompasses a kit for enzyme cycling method including an enzyme labeled with a reactive carrier, a substrate thereof, an enzyme for cycling reaction and thio-NAD and NADH as a co-enzyme thereof. The reactive carrier represents an antibody, a nucleic acid probe, lectin and the like having a binding activity to a measuring subject. The reactive carrier is not particularly limited if it is a material suitable for the measuring subject, or a material suitable for the labeling enzyme and the substrate thereof.

More specifically, the present invention encompasses a kit for enzyme cycling method including a labeling enzyme, a substrate thereof, an enzyme for cycling reaction and thio-NAD and NADH as a co-enzyme thereof.

The kit of the present invention is a kit for enzyme immunoassay including reagents (1) to (5) below:

(1) alkaline phosphatase (ALP), glucosidase, galactosidase, fructosidase, mannosidase or peroxidase, which enzymes are labeled with an antibody specific to a target protein antigen, (2) androsterone derivative represented by the formula (1), which is a substrate of the enzyme, (3) Dehydrogenase (DH), (4) NADH and/or NADPH, and (5) Thio-NAD and/or thio-NADP.

Furthermore, the present invention is a kit for measuring a nucleic acid probe, which includes reagents (1) to (5) below:

(1) alkaline phosphatase (ALP), glucosidase, galactosidase, fructosidase, mannosidase or peroxidase, which enzymes are labeled with a nucleic acid probe specifically binding to a target nucleic acid, (2) androsterone derivative represented by the formula (1), which is a substrate of the enzyme, (3) Dehydrogenase (DH), (4) NADH and/or NADPH, and (5) Thio-NAD and/or thio-NADP.

For the labeling enzyme, the dehydrogenase (DH) and the androsterone derivative represented by the formula (1), can be used are those described above in the method of the present invention as they are.

The kit of the present invention can be a commercial enzyme-labeled antibody and the like in combination with the reagents constituting this kit. This kit can be used in an enzymatic immunoassay using enzyme cycling method.

EXAMPLES

Hereinafter, this invention will be described based on Examples. However, such Examples can be modified variously in the technical level of this field. Needless to say, this invention is not intended to be limited to these Examples only, in light of such technical level. Hereinafter, the present invention will be more specifically described in the following Examples.

Assay of alkaline phosphatase and Pumilio using thio-NAD cycling of system of alkaline phosphatase (ALP) and androsterone 3-phosphate (A3P) as detection system.

Reference Example 1

Manufacture of ALP-Labeled Antibody

A mouse-derived monoclonal antibody having antigen-specific reactivity was dialyzed three times with 0.1 M citric acid buffer solution (pH 3.5) for 30 minutes. The antibody solution was added with pepsin to 0.5% with respect to the amount of the antibody, stood at 37° C. for 1 hour, and then adjusted to neutral pH with 1.5 M Tris buffer solution (pH 8.8). This mixed reaction solution was gel-filtered using a column filled with Superdex 200 (Amersham Biosciences, Inc.), to give F(ab')$_2$. ALP was labeled by ALP-labeling kit (DOJINDO LABORATORIES) using 100 μg of this F(ab')$_2$.

Reference Example 2

Preparation of Insoluble Carrier Immobilized with Antibody 1

A solution of a guinea pig-derived polyclonal antibody having antigen-specific reactivity dissolved in 50 mM sodium carbonate buffer solution (pH 9.6) in a concentration of 100 μg/mL, was added to each well of a flat-bottomed microplate (Nunc A/S) by 50 μL each, and stood at room temperature for 1 hour, and then the antibody solution was collected. 300 μL of TBS containing 2% bovine serum albumin (BSA) was added and stood at room temperature for 2 hours to perform the blocking treatment, to give a polyclonal antibody-immobilized microplate.

Reference Example 3

Preparation of Insoluble Carrier Immobilized with Antibody 2

A solution of a guinea pig-derived polyclonal antibody having antigen-specific reactivity dissolved in 50 mM sodium carbonate buffer solution (pH 9.6) in a concentration of 10 μg/mL was added to each well of a flat-bottomed microplate (Nunc NS) by 50 μL each, and stood at room temperature for 1 hour. Then, the solution in the well was removed with suction, 300 μL of TBS containing 0.1% bovine serum albumin (BSA) was added and stood at room temperature for 2 hours to perform the blocking treatment, and washed with TBS containing 0.05% Tween 20, to give a polyclonal antibody-immobilized microplate.

Comparative Example 1

Assay of Pumilio by One Step Method using 5α-Androsterone 3-Phosphate

Reaction Test Solution 0.2 M glycine buffer solution (pH 8.8); 1.5 mM thio-NAD; 1 mM NADH; 0.5 mM 5α-androsterone 3-phosphate; 20 U/mL 3α-hydroxysteroid dehydrogenase.

Sample for Assay 0.1, 0.5, 1, 2, 5, 10, 50, 100 and 200 ng/mL Pumilio

Method for Assay

Figure 2:
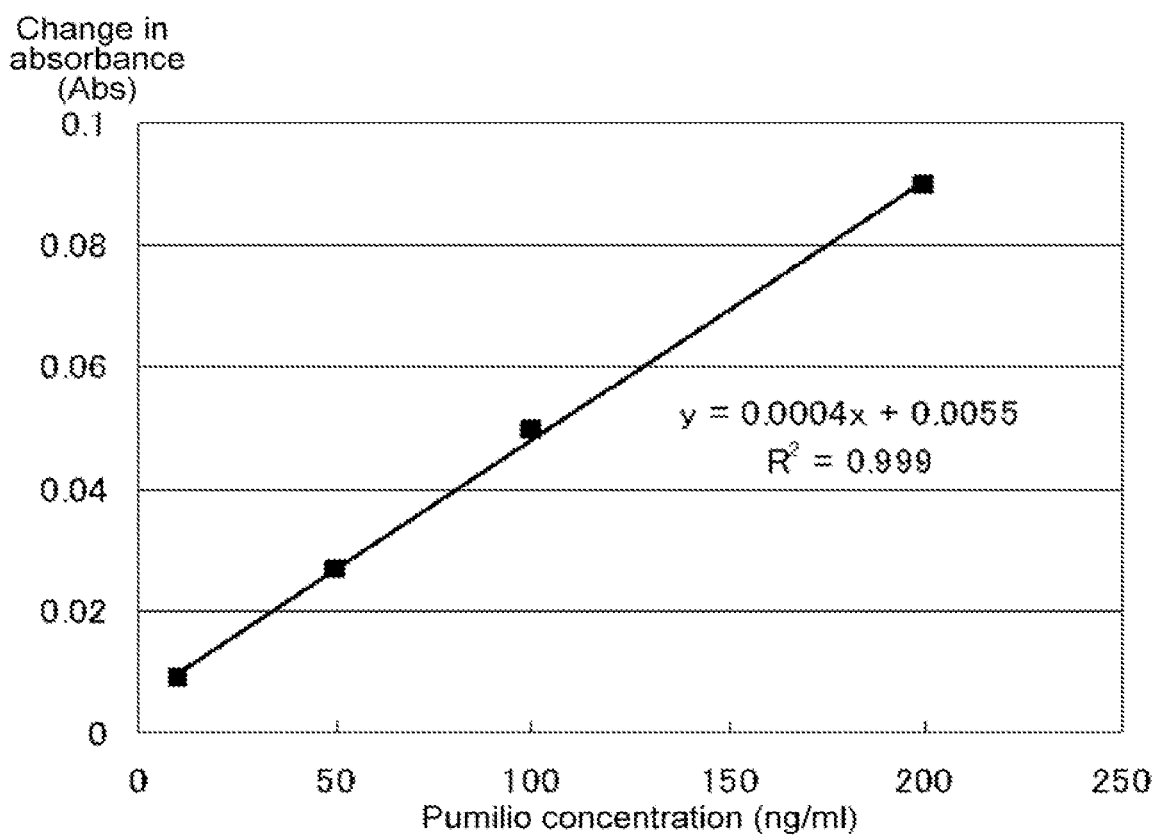
FIG. 2 is the calibration curve of Pumilio obtained in Comparative Example 1.

To a microplate immobilized with the anti-Pumilio guinea pig polyclonal antibody prepared with the method of Reference Example 2, 50 μL of TBS (pH 7.5) containing 0.1% BSA solution containing purified Pumilio (standard substance) in a range of 0 to 200 ng/ml was added, and the microplate was stirred at room temperature for 1 hour. Then, the solution in the well was removed with suction, and then the microplate was washed with TBS (pH 7.5) containing 0.05% Tween 20. The microplate was added with 50 μL of TBS (pH 7.5) containing 0.1% BSA solution containing the ALP-labeled anti-Pumilio mouse monoclonal antibody prepared with the method of Reference Example 1 in a concentration of 2.5 μg/ml, and the microplate was stirred for 1 hour. The solution in the well was removed with suction, and then the microplate was washed with TBS (pH 7.5) containing 0.05% Tween 20, and further washed with TBS. Then, 100 μL of the reaction test solution was added to each well, respectively, and the absorbance was measured for 30 minutes using a 405 nm filter with a microplate reader (MTP-500 manufactured by CORONA CORPORATION)

while warming the microplate to 37° C. The amount of the absorbance change for 30 minutes was plotted with respect to the concentrations of the standard substance. The obtained straight line well-dependent on the concentration is shown in FIG. 2.

Herein, poor reactivity of the enzyme (alkaline phosphatase) with the substrate (androsterone 3-phosphate), and inhibition of the substrate on the cycling reaction came up as problems, and thus two-step method in which the enzyme reaction and the cycling reaction are split, was tried. In addition, it was found out that 3α-hydroxysteroid dehydrogenase, in the cycling reaction an enzyme had phosphatase activity, and was a cause for the blank, and thus it was determined to use a buffer solution containing phosphoric acid at the time of the cycling reaction of the two-step method.

Comparative Example 2

Figure 3:
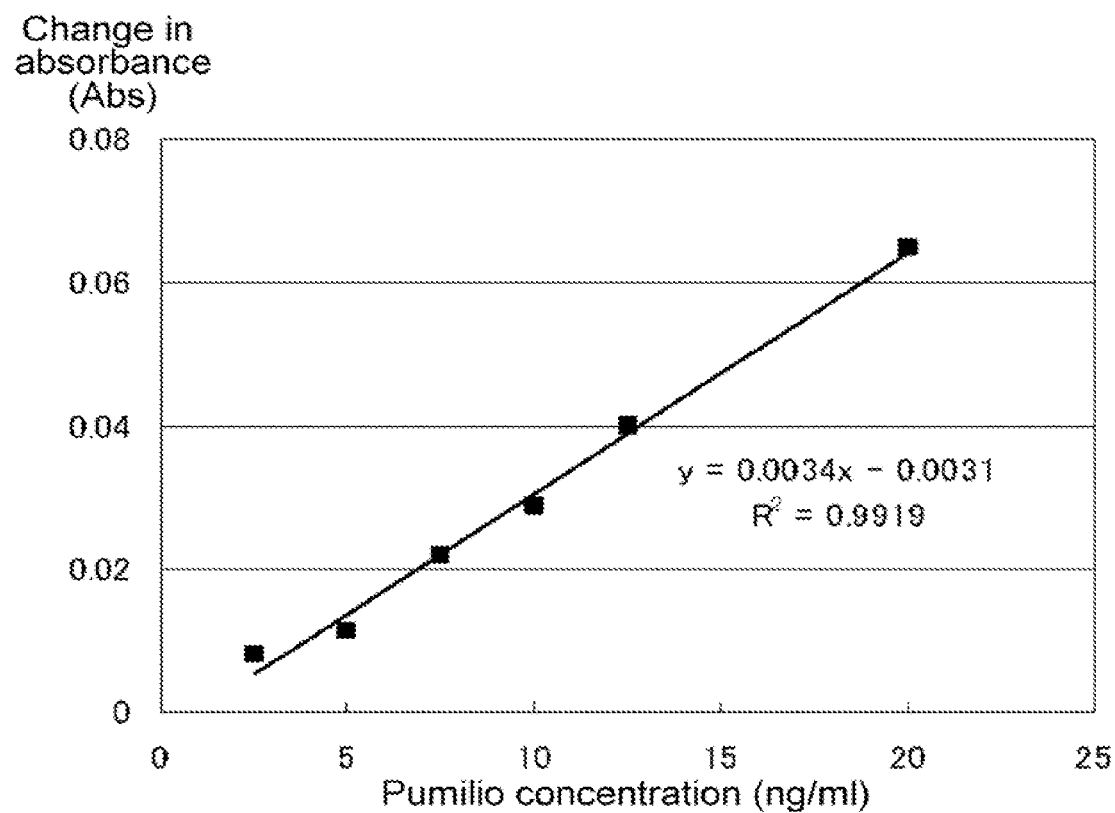
FIG. 3 is the calibration curve of Pumilio obtained in Comparative Example 2.

Assay of Pumilio by Two-Step Method using 5α-Androsterone 3-Phosphate
Reaction Test Solution A
0.1 M Tris buffer solution (pH 8.3); 1 mM $MgCl_2$; 0.1 mM 5α-androsterone 3-phosphate.
Reaction Test Solution B
0.2 M disodium hydrogen phosphate-containing 0.2 M glycine buffer solution (pH 9.6); 3 mM thio-NAD; 1 mM NADH; 40 U/mL 3α-hydroxysteroid dehydrogenase
Sample for Assay
0.5, 0.75, 1, 2.5, 5, 7.5, 10, 12.5, 20, 50, 75, and 100 ng/ml Pumilio
Method for Assay
To a microplate immobilized with the anti-Pumilio guinea pig polyclonal antibody prepared in the method of Reference Example 3, 50 μL of TBS (pH 7.5) containing 0.1% BSA solution containing purified Pumilio (standard substance) in a range of 0 to 100 ng/mL was added, and the microplate was stirred at room temperature for 1 hour. Then, the solution in the well was removed with suction, and then the microplate was washed with TBS (pH 7.5) containing 0.05% Tween 20. The microplate was added with 50 μL of TBS (pH 7.5) containing 0.1% BSA solution containing the ALP-labeled anti-Pumilio mouse monoclonal antibody prepared in the method of Reference Example 1 in a concentration of 2.5 μg/mL, and the microplate was stirred for 1 hour. The solution in the well was removed with suction, and then the microplate was washed with TBS (pH 7.5) containing 0.05% Tween 20, and further washed with TBS. Then, 50 μL of Reaction test solution A was added to each well, respectively, and the microplate was incubated at 37° C. for 30 minutes. Subsequently, 50 μL of Reaction Test Solution B was added to the well, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 3.

Although the two-step method was tried, the sensitivity did not increase as much as expected, and thus, it was determined to use 5β-androsterone 3-phosphate, which has different structure from that of 5α-androsterone 3-phosphate used so far, in order to improve the reactivity with alkaline phosphatase.

Comparative Example 3

Figure 4:
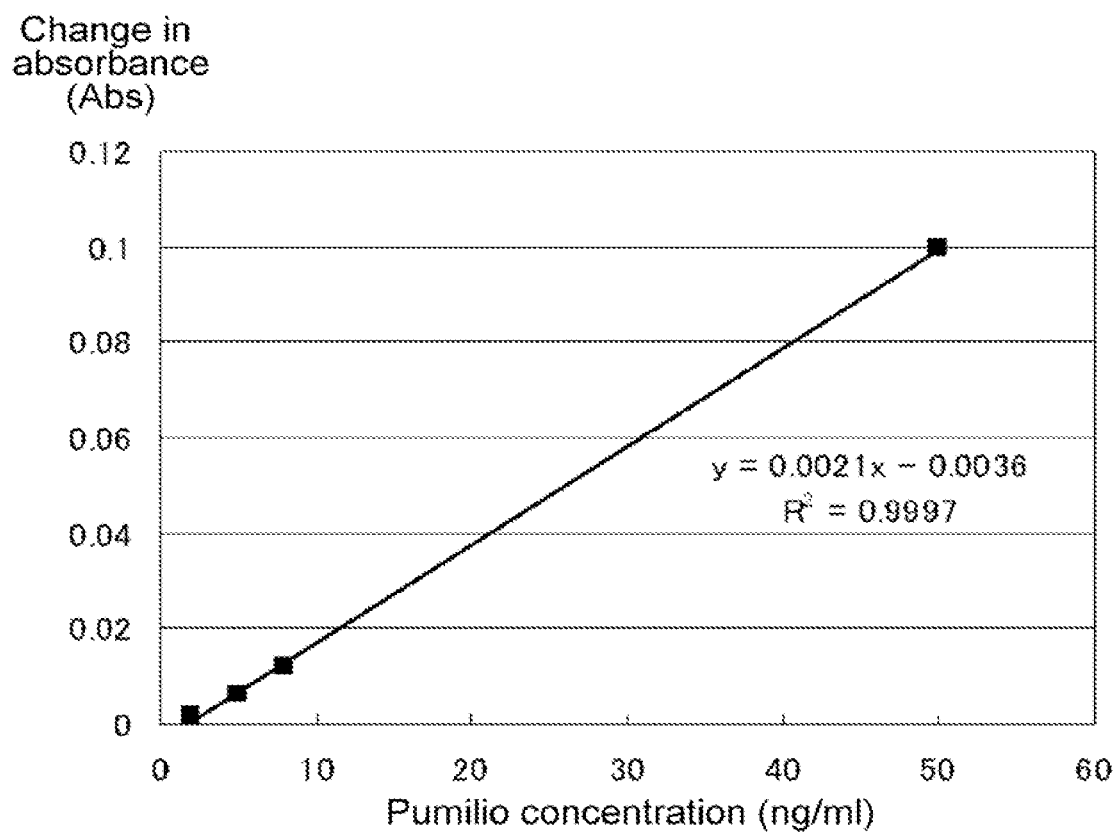
FIG. 4 is the calibration curve of Pumilio obtained in Comparative Example 3.

Assay of Pumilio by One Step Method using 5β-Androsterone 3-Phosphate
Reaction Test Solution
0.1 M Tris buffer solution (pH 8.6); 0.5 mM $MgCl_2$; 1.5 mM thio-NAD; 0.5 mM NADH; 0.5 mM 5β-androsterone 3-phosphate; 20 U/mL 3α-hydroxysteroid dehydrogenase.
Sample for Assay
0.1, 0.5, 1, 2, 5, 8, 10, 20 and 50 ng/mL Pumilio
Method for Assay
To a microplate immobilized with the anti-Pumilio guinea pig polyclonal antibody prepared in the method of Reference Example 3, 50 μL of TBS (pH 7.5) containing 0.1% BSA solution containing purified Pumilio (standard substance) in a range of 0 to 50 ng/ml was added, and the microplate was stirred at room temperature for 1 hour. Then, the solution in the well was removed with suction, and then the microplate was washed with TBS (pH 7.5) containing 0.05% Tween 20. 50 μL of TBS (pH 7.5) containing 0.1% BSA solution containing the ALP-labeled anti-Pumilio mouse monoclonal antibody prepared in the method of Reference Example 1 in a concentration of 2.5 μg/mL was added, and the microplate was stirred for 1 hour. The solution in the well was removed with suction, and then the microplate was washed with TBS (pH 7.5) containing 0.05% Tween 20, and further washed with TBS. Then, to each well, 50 μL of the reaction test solution was added, respectively, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 4.

Comparative Example 4

Figure 5:
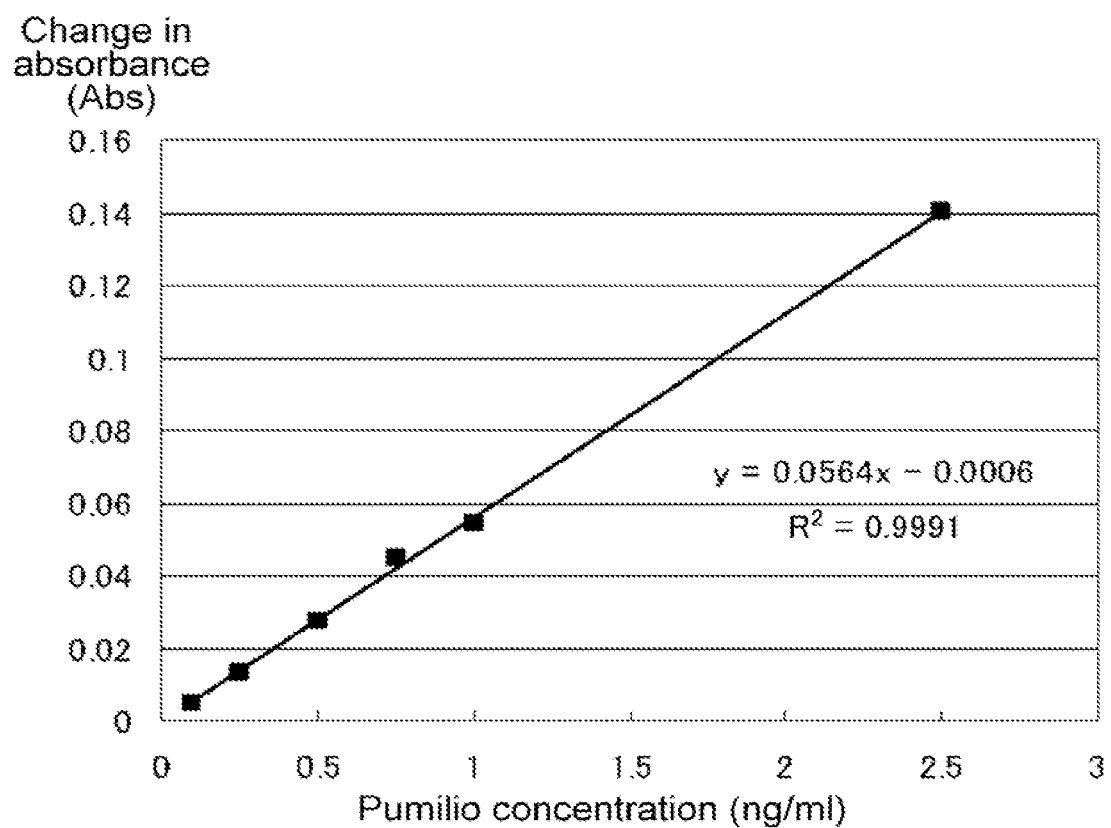
FIG. 5 is the calibration curve of Pumilio obtained in Comparative Example 4.

Assay of Pumilio by Two-Step Method using 5β-Androsterone 3-Phosphate
Reaction Test Solution A
0.1 M Tris buffer solution (pH 8.3); 1 mM $MgCl_2$; 0.1 mM 5β-androsterone 3-phosphate.
Reaction Test Solution B
0.2 M disodium hydrogen phosphate-containing 0.2 M glycine buffer solution; 3 mM thio-NAD; 1 mM NADH; 40 U/mL 3α-hydroxysteroid dehydrogenase
Sample for Assay
0.005, 0.01, 0.05, 0.1, 0.25, 0.5, 0.75, 1, 2.5, 5, 10, 25 and 50 ng/ml Pumilio
Method for Assay
To a microplate immobilized with the anti-Pumilio guinea pig polyclonal antibody prepared in the method of Reference Example 3, 50 μL of TBS (pH 7.5) containing 0.1% BSA solution containing purified Pumilio (standard substance) in a range of 0 to 50 ng/mL was added, and the microplate was stirred at room temperature for 1 hour. Then, the solution in the well was removed with suction, and then the microplate was washed with TBS (pH 7.5) containing 0.05% Tween 20. The microplate was added with 50 μL of TBS (pH 7.5) containing 0.1% BSA solution containing the ALP-labeled anti-Pumilio mouse monoclonal antibody prepared in the method of Reference Example 1 in a concentration of 2.5 μg/mL, and the microplate was stirred for 1 hour. The solution in the well was removed with suction, and then the microplate was washed with TBS (pH 7.5) containing 0.05% Tween 20, and further washed with TBS. Then, 50 μL of Reaction Test Solution A was added to each well, respectively, and the microplate was incubated at 37° C. for 30 minutes. Subsequently, 50 μL of Reaction Test Solution B was added to the well, and the absorbance was measured for 10 minutes using a 405 nm filter with a microplate reader (MTP-500 manufactured by CORONA CORPORATION) while warming the microplate to 37° C. The amount of the absorbance change for 10 minutes was plotted with respect to the concentrations of the standard substance. The obtained straight line well-dependent on the concentration is shown in FIG. 5.

Figure 6:
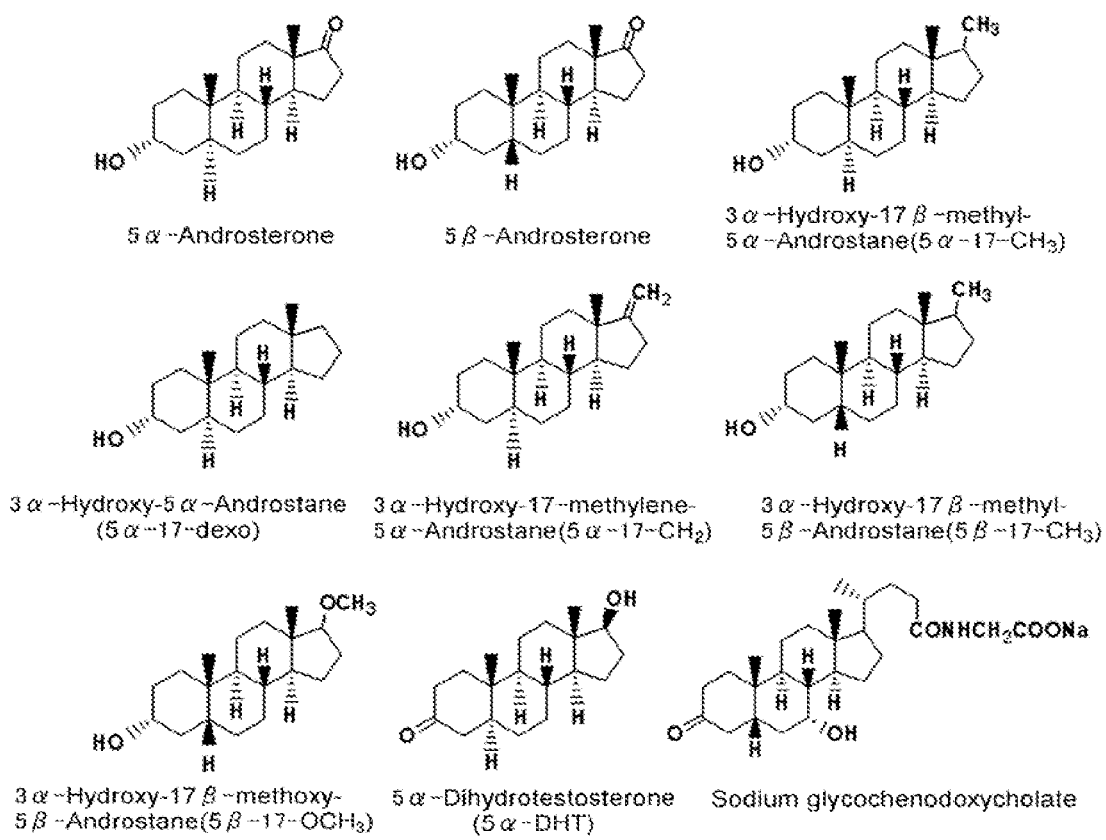
FIG. 6 is example compounds of some 3α-hydroxyandrostane.

It was found out that androsterone 3-phosphate was a substrate of the cycling reaction so far, and blank increase by this result became a problem. It was ascertained that the cause was ketone at the position 17, and thus it was determined to use a substrate in which the ketone at the position 17 is removed or substituted. Synthesized 3α-hydroxyandrostanes are shown in FIG. 6. In addition, the rotation numbers of the cycling reactions using them as a substrate are shown in Table 2. Among them, the rotation number of 5α-androsterone was the maximum, and a substrate being close to this were 3α-hydroxy-17β-methoxy-5β-androstane and 5α-dihydrotestosterone. Thus, a phosphate ester of the former, that is, 3α-hydroxy-17β-methoxy-5β-androstane 3-phosphate was synthesized and applied to the thio-NAD cycling.

TABLE 2

Rotation numbers of cycling reactions with 3α-hydroxyandrostanes

| | Cycle/min | Relative value (%) |
|---|---|---|
| 5α-Androsterone | 623 | 100 |
| 5β-Androsterone | 384 | 62 |
| 5α-17-CH$_3$ | 200 | 32 |
| 5α-17-deoxo | 241 | 39 |
| 5α-17-CH$_2$ | 308 | 49 |
| 5β-17-CH$_3$ | 114 | 18 |
| 5β-17β-OCH$_3$ | 458 | 74 |
| 5α-DHT | 535 | 86 |
| Glycochenodeoxycholate (Reference Example) | 129 | 21 |

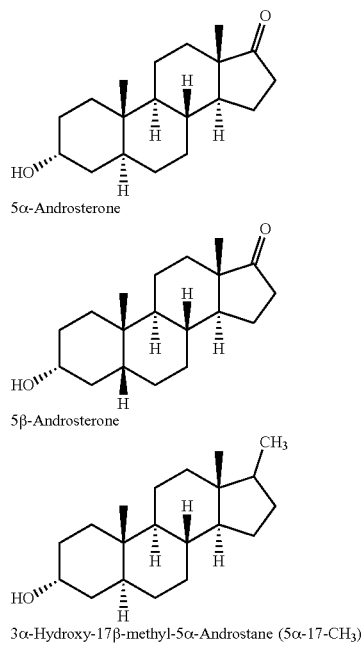

TABLE 2-continued

Rotation numbers of cycling reactions with 3α-hydroxyandrostanes

Cycle/min    Relative value (%)

Example 1

Assay of Alkaline Phosphatase by One Step Method using 3α-Hydroxy-17β-Methoxy-5β-Androstane 3-Phosphate Synthesis of 3α-Hydroxy-17β-Methoxy-5β-Androstane 3-Phosphate To an anhydrous pyridine solution (4 mL) of phosphorus oxychloride (0.26 mL), an anhydrous pyridine solution (4 mL) containing of 3α-hydroxy-17β-methoxy-5β-androstane (200 mg) was dropped under ice cooling, and the reaction solution was stirred further for 1 hour under ice cooling. The reaction solution was poured into ice water, and the solution was alkalinized strongly (about pH 11), and then washed with ether. Then, concentrated hydrochloric acid was added with the aqueous layer to adjust pH to about 2, and then extracted with ether. The ether layer was dried with anhydrous sodium sulfate, and then the solvent was distilled off under reduced pressure. The residue was recrystallized with tetrahydrofuran-hexane to give a colorless crystal (210 mg).

$^1$H-NMR (400 MHz, Methanol-d4) δ=0.73 (s, 3H, 18-CH$_3$), 0.95 (s, 3H, 19-CH$_3$), 3.19 (1H, t, J=8.6 Hz, 17α-H), 3.32 (s, 3H, —OCH$_3$), 4.18 (m, 1H, 3β-H); ESI-HR-MS Calculated for $C_{20}H_{35}O_5P$—H: m/z 385.2149 [M–H]$^-$. Found m/z 385.2157; m.p. 187-188° C.

Reaction Test Solution 0.1 M Tris buffer solution (pH 9.5); 0.2 mM MgCl$_2$; 0.6 mM thio-NAD; 4 mM NADH; 0.5 mM 3α-hydroxy-17β-methoxy-5β-androstane 3-phosphate; 20 U/mL 3α-hydroxysteroid dehydrogenase.

Samples for Assay 0.1, 0.2, 0.5, 1, and 2 mU/mL alkaline phosphatase (final concentration: 0.05, 0.1, 0.25, 0.5, and 1 mU/mL)

Method for Assay

Figure 7:
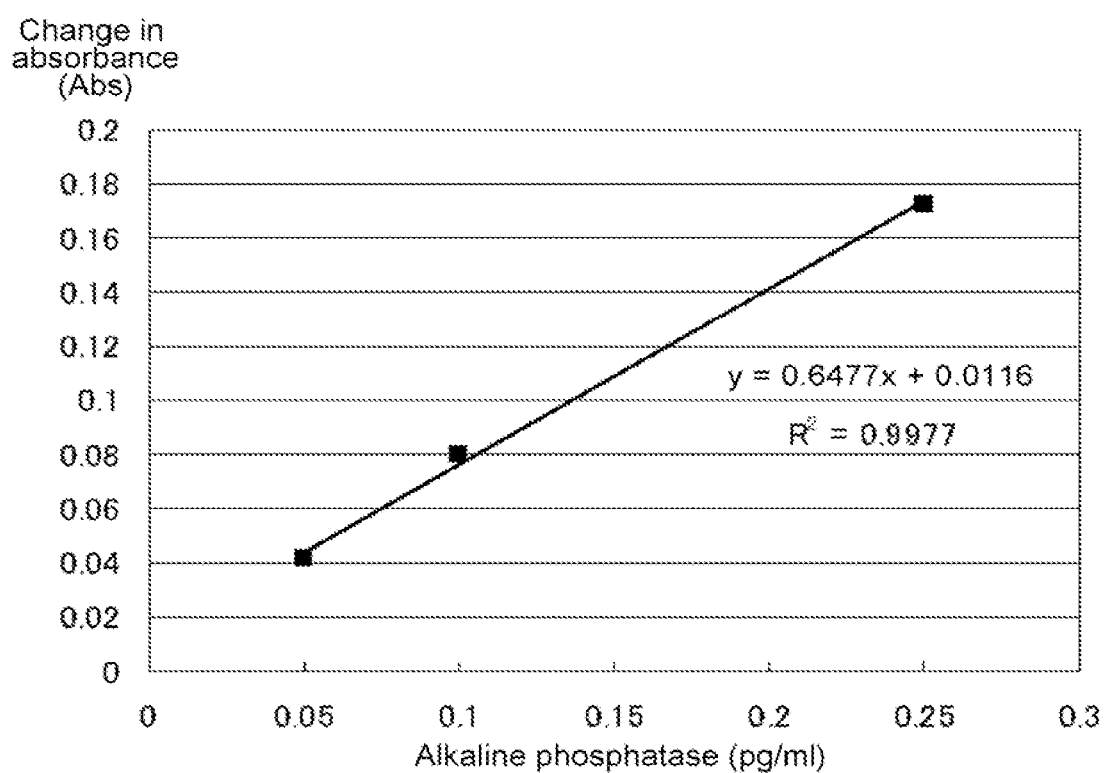
FIG. 7 is the calibration curve of alkaline phosphatase obtained in Example 1.

To a flat-bottomed microplate well, 50 μL of Tris buffer solution (pH 9.5) containing the standard substance (alkaline phosphatase) in a range of 0 to 2 mU/mL was added, and subsequently, 50 μl of Reaction Test Solution B was added to each well, respectively. Then, the absorbance was measured for 60 minutes using a 405 nm filter with a microplate reader (MTP-500 manufactured by CORONA CORPORATION) while warming the microplate to 37° C. The amount of the absorbance change for 60 minutes was plotted with respect to the concentrations of the standard substance. The obtained straight line well-dependent on the concentration is shown in FIG. 7.

Subsequently, which is an enzyme of the cycling reaction in respect of investigation of the two-step method, as described above, a buffer solution containing phosphoric acid was used at the time of the cycling reaction in order to inhibit the phosphatase activity in 3α-hydroxysteroid dehydrogenase. However, a buffer solution containing pyrophosphoric acid rather than the buffer solution containing phosphoric acid was adopted as a buffer solution further inhibiting this phosphatase activity.

Example 2

Assay of Alkaline Phosphatase by Two-Step Method using 3α-Hydroxy-17β-Methoxy-5β-Androstane 3-Phosphate Reaction Test Solution A 0.1 M Tris buffer solution (pH 9.5); 0.2 mM MgCl$_2$; 1 mM 3α-hydroxy-17β-methoxy-5β-androstane 3-phosphate Reaction Test Solution B 0.15 M pyrophosphate buffer solution (pH 9.5); 3 mM thio-NAD; 1 mM NADH; 40 U/mL 3α-hydroxysteroid dehydrogenase Sample for Assay 1, 5, 10, 15, 20 μU/mL alkaline phosphatase (final concentration: 0.5, 2.5, 5, 7.5, and 10 μU/mL)

Method for Assay

Figure 8:
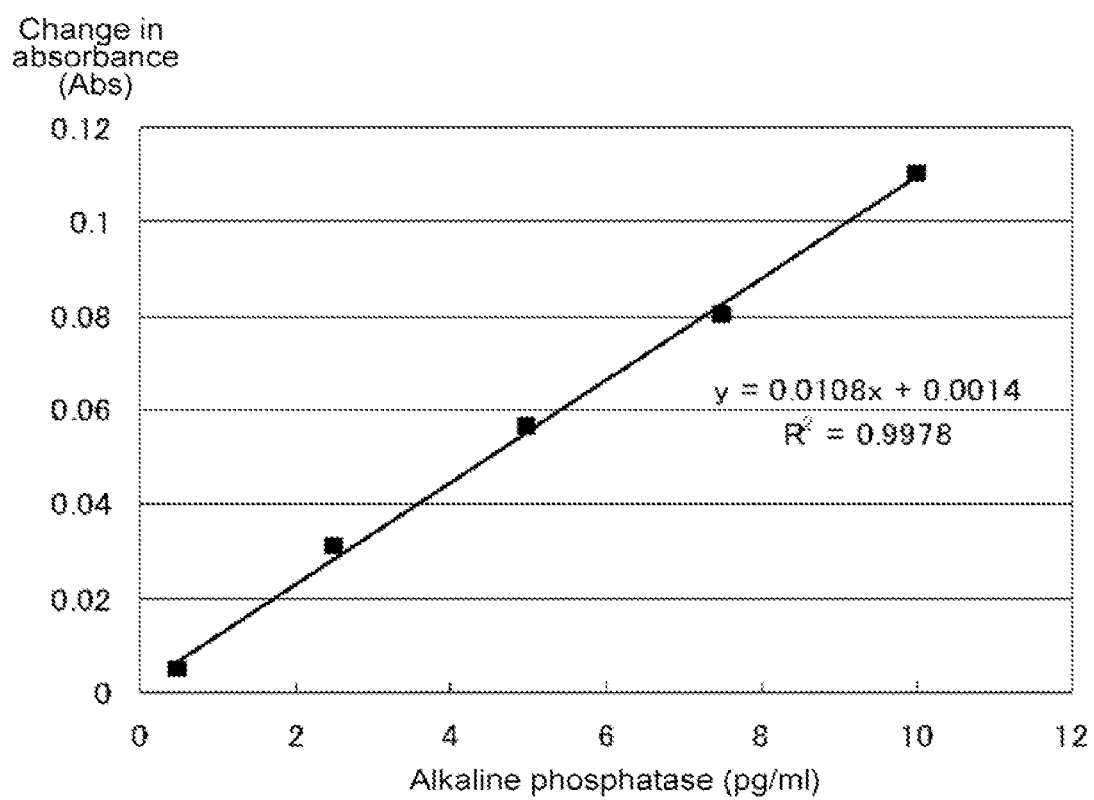
FIG. 8 is the calibration curve of alkaline phosphatase obtained in Example 2.

To a flat-bottomed microplate well, 25 μL of Tris buffer solution (pH 9.5) containing the standard substance (alkaline phosphatase) in a range of 0 to 20 μU/mL was added, and subsequently, 25 μL of Reaction test solution A was added to the well, respectively. The reaction solution was mixed, and stood at 37° C. in an incubator for 1 hour. Then, 50 μL of Reaction Test Solution B was added to each well, respectively, and the absorbance was measured for 20 minutes using a 405 nm filter with a microplate reader (MTP-500 manufactured by CORONA CORPORATION) while warming the microplate to 37° C. The amount of the absorbance change for 20 minutes was plotted with respect to the concentrations of the standard substance. The obtained straight line well-dependent on the concentration is shown in FIG. 8.

Reference Example 4

Purification of Alkaline Phosphatase (ALP)-Labeled Antibody

ALP-labeled antibody was prepared using ALP-labeling-kit (DOJINDO LABORATORIES) from 150 μg of F(ab')$_2$ prepared in Reference Example 1. Since this ALP-labeled antibody solution contained various complexes having various molecular weight of ALP and Fab, and above solution had variation in the activity, the prepared ALP-labeled antibody solution was gel-filtered using Superdex-200 column (Amersham Biosciences, Inc.) filled with Tris buffer solution (pH 7.0) containing 1 mM MgCl$_2$, 0.1 mM ZnCl$_2$ and 0.01% BSA as an elution solution, and the activity of each fraction was compared, and then only ALP-labeled antibody having great S/N ratio was collected.

Reference Example 5

Preparation of Insoluble Carrier Immobilized with Antibody

A solution of a guinea pig-derived polyclonal antibody having antigen-specific reactivity dissolved in 50 mM sodium carbonate buffer solution (pH 9.6) in a concentration of 10 μg/mL was added to each well of a flat-bottomed microplate (Nunc A/S) by 50 μl each, and stood at room temperature for 1 hour, and then the solution in the well was removed with suction, and washed with TBS (pH 7.5) containing 0.5% Triton X-100. Then, 200 μl of TBS containing 5% bovine serum albumin (BSA) was added and stood at 4° C. for 2 hours to overnight to perform the blocking treatment, and was washed with TBS (pH 7.5) containing 0.5% Triton X-100, to give a microplate immobilized with the polyclonal antibody.

Example 3

Assay of Pumilo by One Step Method

Figure 9:
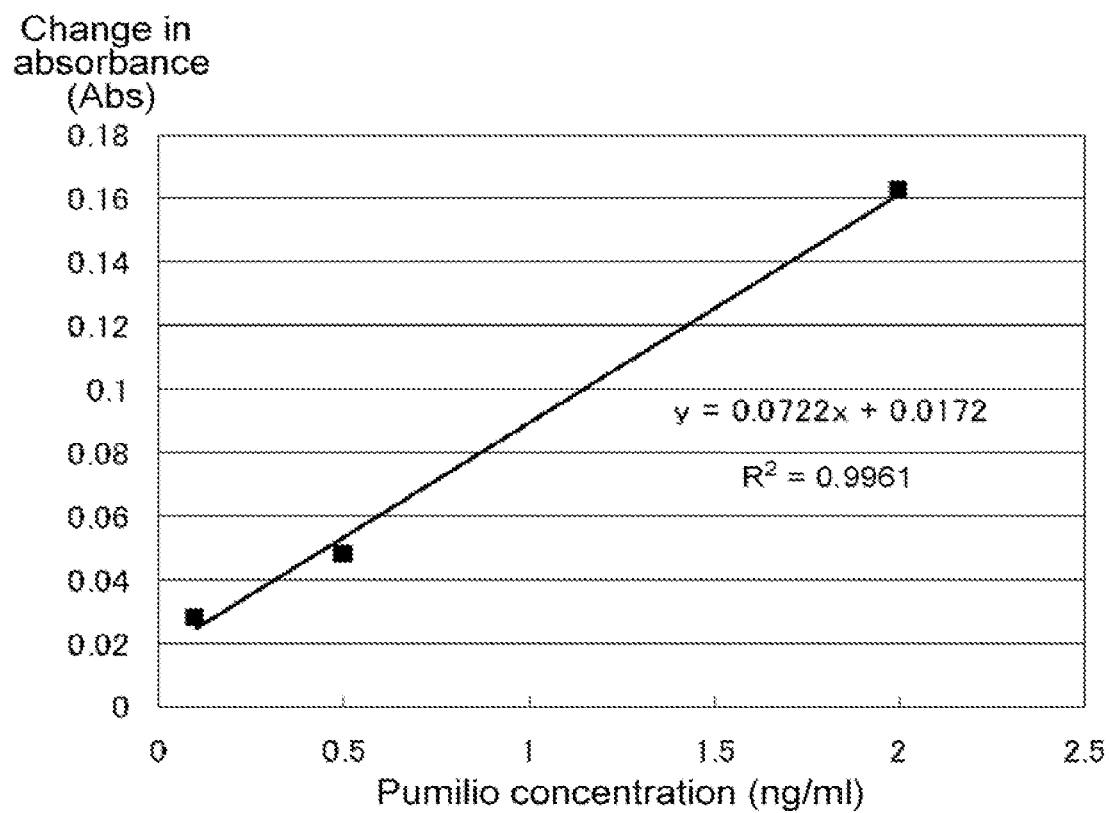
FIG. 9 is the calibration curve of Pumilio obtained in Example 3.

Reaction Test Solution using 3α-Hydroxy-17β-Methoxy-5β-Androstane 3-Phosphate 0.1 M Tris buffer solution (pH 9.5); 1.5 mM thio-NAD; 2.5 mM NADH; 0.1 mM 3α-hydroxy-17β-methoxy-5β-androstane 3-phosphate; 20 U/mL 3α-hydroxysteroid dehydrogenase Sample for Assay 0.1, 0.5, 2, 5, 10 and 25 ng/ml Pumilio Method for Assay To a microplate immobilized with the anti-Pumilio guinea pig polyclonal antibody prepared in the method of Reference Example 5, 50 μL of TBS (pH 7.5) containing 0.1% BSA solution containing purified Pumilio (the standard substance) in a range of 0 to 25 ng/mL was added, and the microplate was stirred at room temperature for 2 hours. Then, the solution in the well was removed with suction, and then the well was washed with TBS (pH 7.5) of containing 0.5% Triton X-100. 50 μL of TBS (pH 7.5) containing 0.1% BSA solution containing the ALP-labeled anti-Pumilio mouse monoclonal antibody prepared in the method of Reference Example 4 in a concentration of approximately 0.8 µg/mL was added, and the microplate was stirred at 4° C. for 2 hours. The solution in the well was removed with suction, and then the well was washed with TBS (pH 7.5) containing 0.5% Triton X-100, and further washed with TBS. Then, to each well, 50 µL of the reaction test solution was added, respectively, and the absorbance was measured for 60 minutes using a 405 nm filter with a microplate reader (MTP-500 manufactured by CORONA CORPORATION) while warming the microplate to 37° C. The amount of the absorbance change for 60 minutes was plotted with respect to the concentrations of the standard substance. The obtained straight line well-dependent on the concentration is shown in FIG. 9.

Example 4

Figure 10:
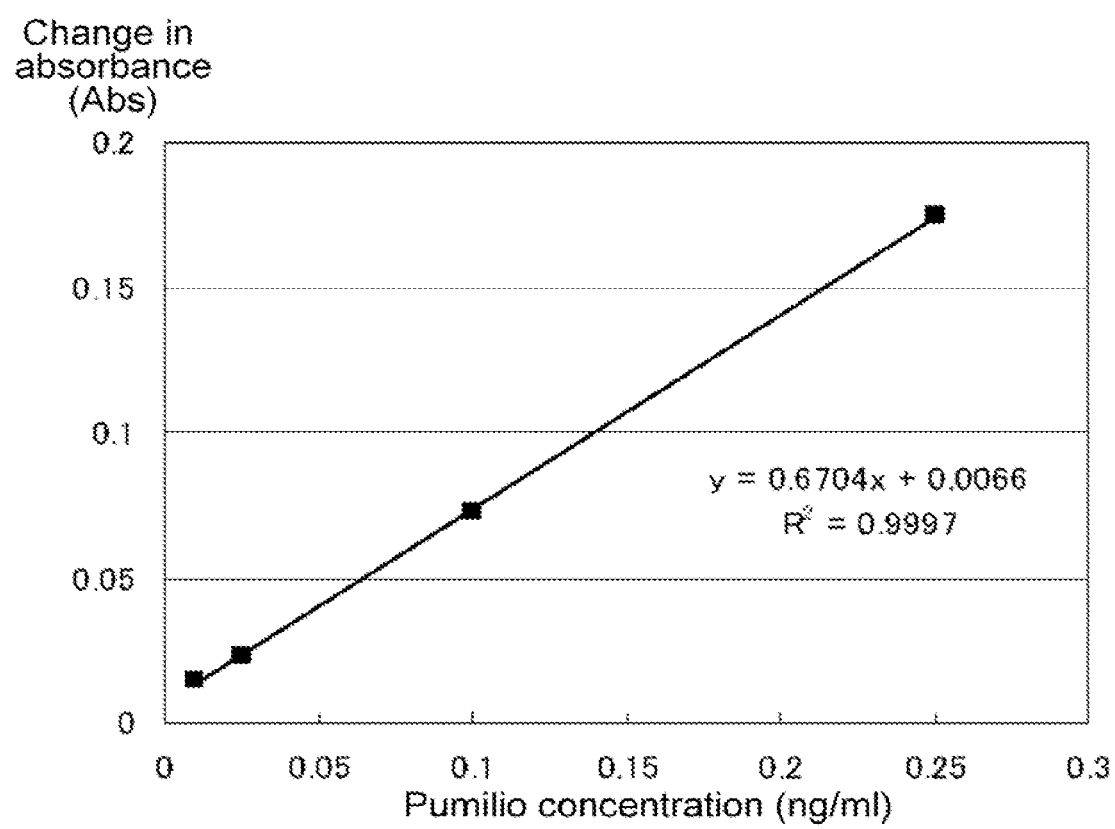
FIG. 10 is the calibration curve of Pumilio obtained in Example 4.

Assay of Pumilio by Two-Step Method using 3α-Hydroxy-17β-Methoxy-5β-Androstane 3-Phosphate Reaction Test Solution A 0.1 M Tris buffer solution (pH 9.5); 0.1 mM $MgCl_2$; 0.2 mM 3α-Hydroxy-17β-Methoxy-5β-Androstane 3-Phosphate Reaction Test Solution B 0.15 M pyrophosphate buffer solution (pH 9.5); 3 mM thio-NAD; 1 mM NADH; 40 U/mL 3α-hydroxysteroid dehydrogenase Sample 0.01, 0.025, 0.05, 0.1, 0.25 and 0.5 ng/ml Pumilio Method for Assay To a microplate immobilized with the anti-Pumilio guinea pig polyclonal antibody prepared with the method of Reference Example 5, 50 µL of TBS (pH 7.5) containing 0.1% BSA solution containing purified Pumilio (the standard substance) in a range of 0 to 0.5 ng/mL was added, and the microplate was stirred at room temperature for 2 hours. Then, the solution in the well was removed with suction, and then the well was washed with TBS (pH 7.5) containing 0.5% Triton X-100. 50 µL of TBS (pH 7.5) containing 0.1% BSA solution containing the ALP-labeled anti-Pumilio mouse monoclonal antibody prepared in the method of Reference Example 4 in approximately 0.2 µg/ml and the rabbit $F(ab')_2$ in a concentration of 1 mg/mL was added, and the microplate was stirred at 4° C. for 2 hours. The solution in the well was removed with suction, and then the residue was washed with TBS (pH 7.5) containing 0.5% Triton X-100, and further washed with TBS. Then, 50 µL of Reaction Test Solution A was added to each well, respectively, and the microplate was incubated at 37° C. for 30 minutes. Subsequently, 50 µL of Reaction Test Solution B was added to the well, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 10.

Although a substrate modified at the position 17 was used, the blank reaction could not be completely removed as described above. Thus, β-galactosidase was used as a labeling enzyme of ELISA, and androsterone β-D-galactoside was synthesized as a substrate thereof, and the investigation proceeded.

Assay of β-galactosidase and Pumilio thio-NAD cycling of system of β-galactosidase and androsterone 3-β-D-galactoside using as detection system.

Example 5

Assay of β-Galactosidase by Two-Step Method using 5β-Androsterone β-D-galactoside Synthesis of 5β-Androsterone-3β-D-Galactoside (Formal Name: 5β-Androsterone 3β-D-Galactopyranoside To a dichloromethane solution (15 mL) of 5β-androsterone (290 mg), MS4A (1.25 g) and phenyl 2,3,4,6-O-tetrabenzoyl-1-thio-β-D-galactopyranoside (1.03 g) were added and the reaction solution was stirred at −20° C. for 15 minutes. Then, the reaction solution was added with N-iodosuccinimide (435 mg) and trifluoromethane sulfonic acid (15 mg), stirred at −20° C. for 2 hours, and then reacted further at room temperature for 2 hours. The reaction solution was added with 250 µL of triethylamine to stop the reaction, and washed with a mixed solution of saturated sodium carbonate and thiosodium sulfate in 3:1, and saturated saline sequentially. The organic layer was dried with anhydrous sodium sulfate, and then the solvent was distilled off under reduced pressure. The residue was dissolved in methanol (15 mL), and added with 28% sodium methoxide (500 µL) and the reaction solution was stirred for 2 hours. The reaction solution was added with acetic acid to be neutralized, and then inspissated under reduced pressure. The residue was purified with silica gel column chromatography (24×240 mm, 10% methanol-chloroform), and then recrystallized with methanol to give a colorless crystal (360 mg).

$^1$H-NMR (400 MHz, Methanol-d4) δ=0.85 (s, 3H, 18-$CH_3$), 0.97 (s, 3H, 19-$CH_3$), 3.44-3.49 (bm, 3H, H-2', H-3', H-5'), 3.70 (d, 1H, H-6'a), 3.72 (d, 1H, H-6'b), 3.73 (m, 1H, 3β-H), 3.81 (d, 1H, H-4'), 4.33 (d, 1H, H-1', $J_{1',2'}$=6.2 Hz); ESI-HR-MS Calculated for $C_{25}H_{40}O_7$—H: m/z 451.2701 [M−H]. Found m/z 451.2711; m.p. 130-135° C.

Reaction Test Solution A 0.1 M phosphate buffer solution (pH 7.3); 0.2 mM $MgCl_2$; 0.1 mM 5β-androsterone β-D-galactoside Reaction Test Solution B 0.1 M pyrophosphate buffer solution (pH 9.0); 1.2 mM thio-NAD; 3.6 mM NADH; 40 U/mL 3α-hydroxysteroid dehydrogenase Sample 1, 4, 10, 40, 100, and 200 pg/ml β-galactosidase (final concentration: 0.5, 2, 5, 20, 50 and 100 pg/mL)

Figure 11:
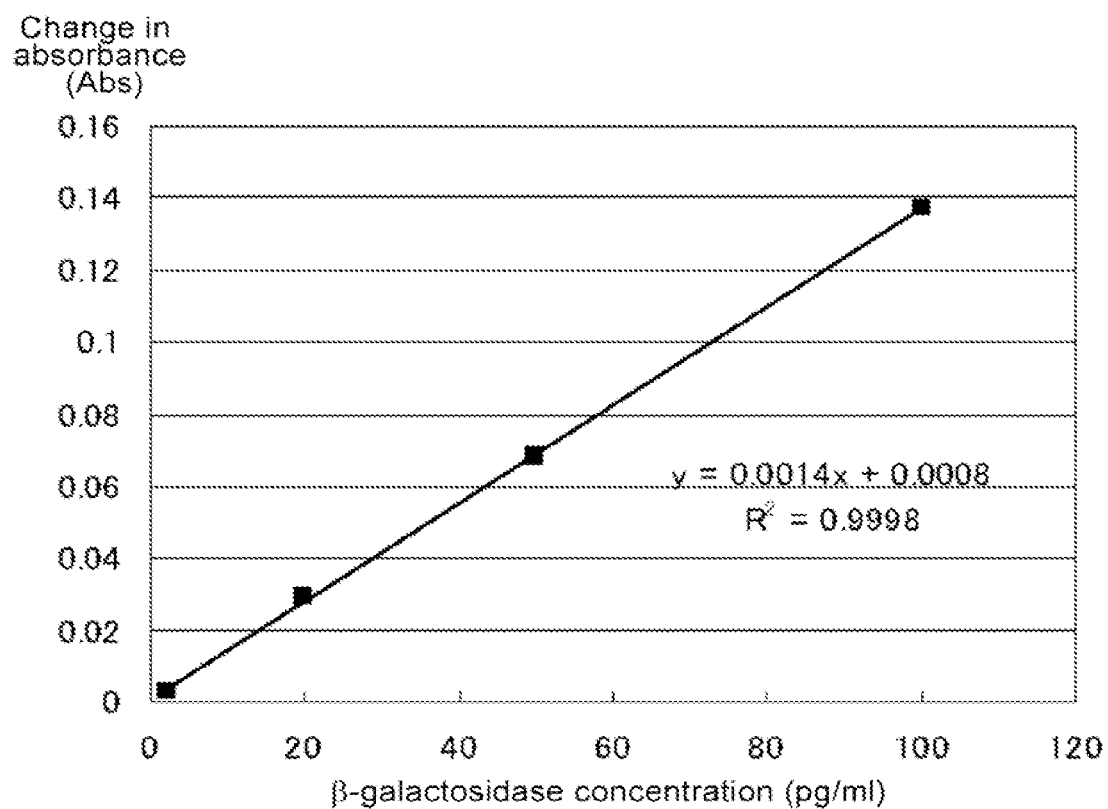
FIG. 11 is the calibration curve of β-galactosidase obtained in Example 5.

To a flat-bottomed microplate well, 25 µL of a phosphate buffer solution (pH 7.3) containing the standard substance (β-galactosidase) in a range of 0 to 200 pg/ml was added, and subsequently, 25 µL of Reaction Test Solution A was added to the well, respectively. The reaction solution was mixed, and the microplate was incubated at 37° C. for 60 minutes. Then, 50 µL of Reaction Test Solution B was added to each well, respectively, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 11.

Example 6

Assay of β-Galactosidase by One-Step Method using 5β-Androsterone β-D-Galactoside Reaction Test Solution 0.1 M phosphate buffer solution (pH 7.7); 10 mM $MgCl_2$; 6 mM thio-NAD; 1 mM NADH; 0.1 mM 5β-androsterone β-D-galactoside; 40 U/mL 3α-hydroxysteroid dehydrogenase Sample 5, 10, 25, 50, 100, and 250 pg/mL β-galactosidase (final concentration: 2.5, 5, 12.5, 25, 50 and 125 pg/mL)

Method for Assay

Figure 12:
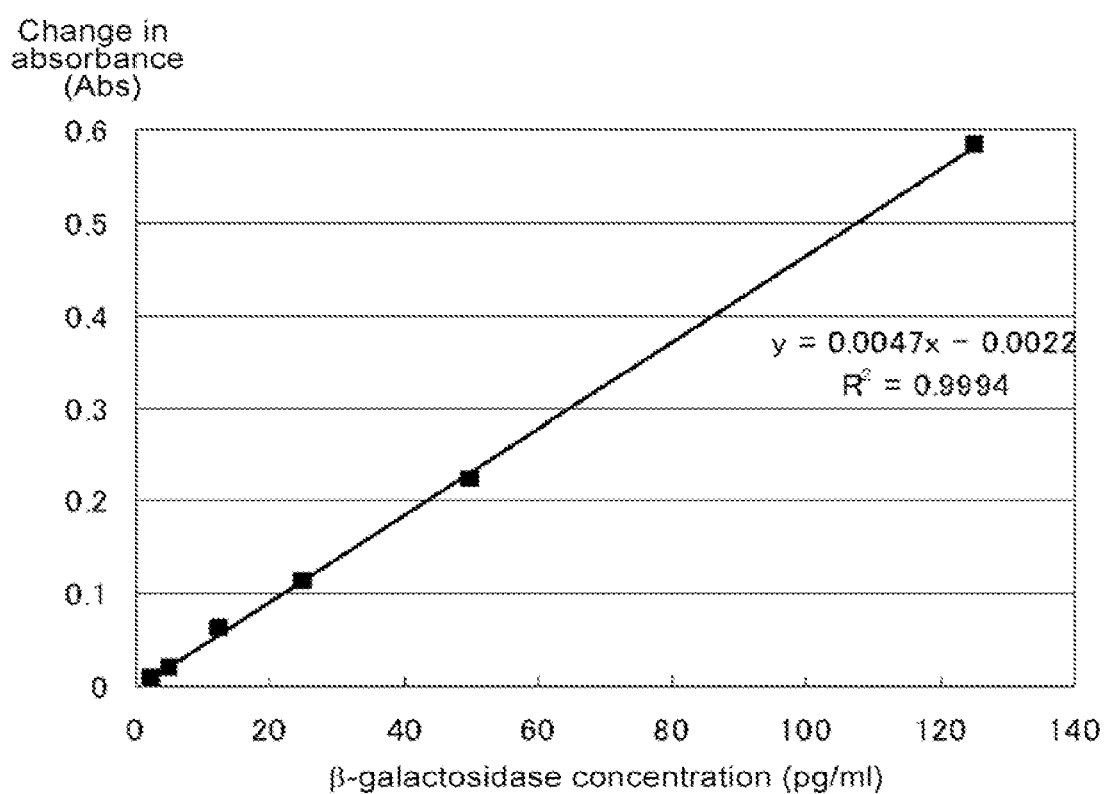
FIG. 12 is the calibration curve of β-galactosidase obtained in Example 6.

To a flat-bottomed microplate well, 50 μL of a phosphate buffer solution (pH 7.7) containing the standard substance (β-galactosidase) in a range of 0 to 250 pg/ml was added, and subsequently, 50 μL of Reaction Test Solution was added to each well, respectively. The absorbance was measured for 120 minutes using a 405 nm filter with a microplate reader (MTP-500 manufactured by CORONA CORPORATION) while warming the microplate to 37° C. The amount of the absorbance change for 120 minutes was plotted with respect to the concentrations of the standard substance. The obtained straight line well-dependent on the concentration is shown in FIG. 12.

Example 7

Assay of β-Galactosidase by Two-Step Method using 5β-Androsterone β-D-Galactoside Reaction Test Solution A 0.1 M phosphate buffer solution (pH 7.5); 10 mM $MgCl_2$; 0.1 mM 5β-androsterone β-D-galactoside Reaction Test Solution B 0.1 M pyrophosphate buffer solution (pH 9.0); 4.8 mM thio-NAD; 0.4 mM NADH; 40 U/mL 3α-hydroxysteroid dehydrogenase Sample 1, 4, 10, 40, 100 and 200 pg/ml β-galactosidase (final concentration: 0.5, 2, 5, 20, 50 and 100 pg/ml)

Method for Assay

Figure 13:
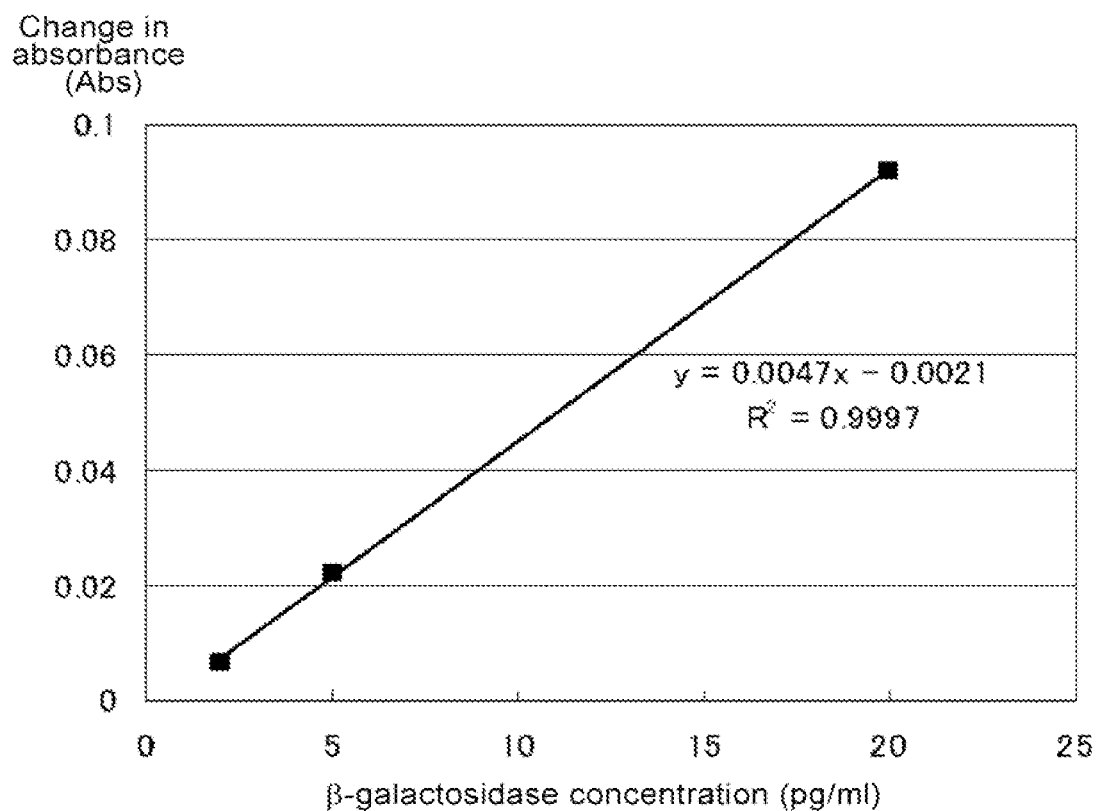
FIG. 13 is the calibration curve of β-galactosidase obtained in Example 7.

To a flat-bottomed microplate well, 25 μL of a phosphate buffer solution (pH 7.5) containing the standard substance (β-galactosidase) in a range of 0 to 200 pg/mL was added, and subsequently, 25 μL of Reaction Test Solution A was added to the well, respectively. The reaction solution was mixed, and the microplate was incubated at 37° C. for 60 minutes. Then, 50 μL of Reaction Test Solution B was added to each well, respectively, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 13.

Example 8

Assay of β-Galactosidase by One-Step Method using 3α-Hydroxy-17β-Methoxy-5β-Androstane β-D-Galactoside Synthesis of 3α-Hydroxy-17β-Methoxy-5β-Androstane β-D-Galactoside (Formal Name: 3α-Hydroxy-17β-Methoxy-5β-Androstane β-D-Galactopyranoside To a dichloromethane solution (15 mL) of 3α-hydroxy-17β-methoxy-5β-androstane (306 mg), MS4A (1.25 g) and phenyl 2,3,4,6-O-tetrabenzoyl-1-thio-P-D-galactopyranoside (1.03 g) were added and the reaction solution was stirred at −20° C. for 15 minutes. Then, N-iodosuccinimide (435 mg) and trifluoromethane sulfonic acid (15 mg) were added; the reaction solution was stirred at −20° C. for 2 hours, and then reacted further at room temperature for 2 hours. The reaction solution was added with 250 μL triethylamine to stop the reaction, and sequentially washed with a mixed solution of saturated sodium carbonate and thiosodium sulfate in 3:1 and saturated saline. The organic layer was dried with anhydrous sodium sulfate, and then the solvent was distilled off under reduced pressure. The residue was dissolved in methanol (15 mL) and added with 28% sodium methoxide (500 μL) and the reaction solution was stirred for 2 hours. The reaction solution was added with acetic acid to be neutralized, and then inspissated under reduced pressure. The residue was purified with silica gel column chromatography (24×240 mm, 10% methanol-chloroform), and then recrystallized with acetone-hexane to give a colorless crystal (383 mg).

$^1$H-NMR (400 MHz, Methanol-d4) δ=0.73 (s, 3H, 18-$CH_3$), 0.95 (s, 3H, 19-$CH_3$), 3.26 (t, 1H, J=8.6 Hz, 17α-H), 3.32 (s, 3H, —$OCH_3$), 3.45-3.51 (bm, 3H, H-2', H-3', H-5'), 3.71 (s, 1H, H-6'a), 3.73 (d, 1H, H-6'b), 3.74 (m, 1H, 3β-H), 3.81 (d, 1H, H-4'), 4.33 (d, 1H, H-1', $J_{1',2'}$=7.5 Hz); ESI-HR-MS Calculated for $C_{26}H_{44}O_7$—H: m/z 467.3014 [M−H]. Found m/z 451.3026. m.p. 197-199° C.

Reaction Test Solution 0.1 M phosphate buffer solution (pH 8.5); 10 mM $MgCl_2$; 6 mM thio-NAD; 1 mM NADH; 0.2 mM 3α-hydroxy-17β-methoxy-5β-androstane β-D-galactoside Sample 5, 10, 25, 50, 100, and 250 pg/mL β-galactosidase (final concentration: 2.5, 5, 12.5, 25, 50 and 125 pg/mL)

Method for Assay

Figure 14:
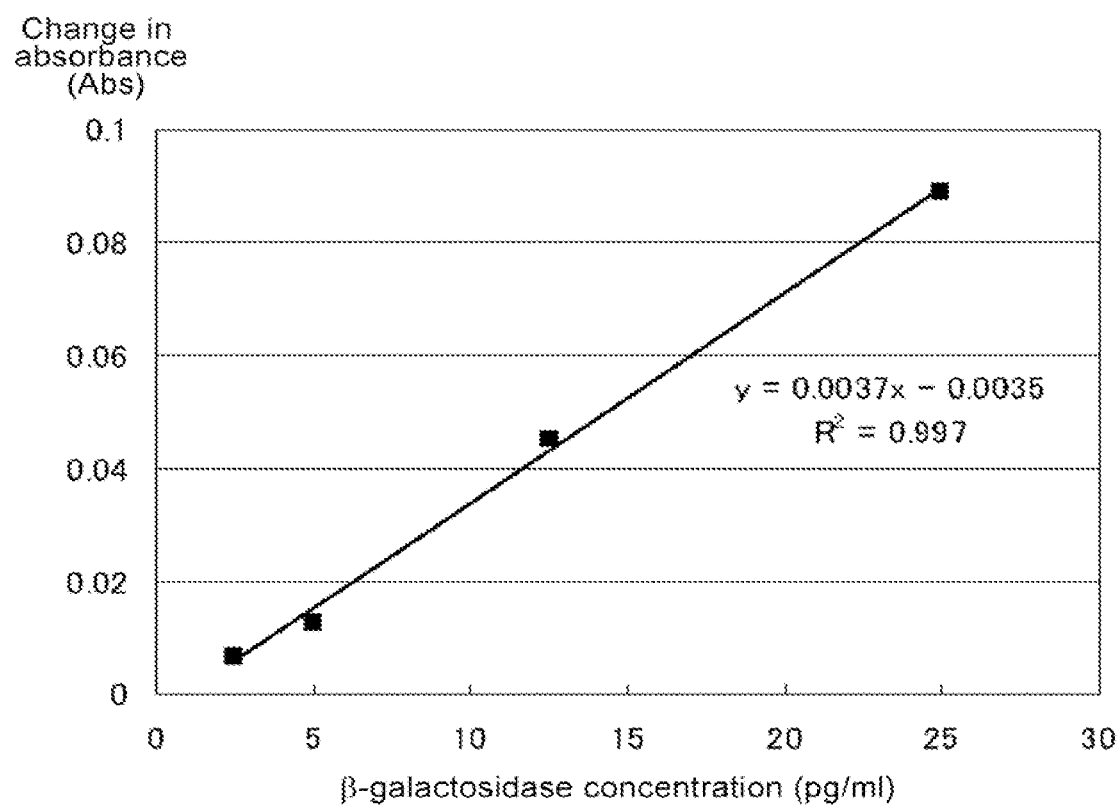
FIG. 14 is the calibration curve of β-galactosidase obtained in Example 8.

To a flat-bottomed microplate well, 50 μL of a phosphate buffer solution (pH 8.5) containing the standard substance ((β-galactosidase) in a range of 0 to 250 pg/mL was added, and subsequently, 50 μL of Reaction Test Solution was added to each well, respectively, and the absorbance was measured for 120 minutes using a 405 nm filter with a microplate reader (MTP-500 manufactured by CORONA CORPORATION) while warming the microplate to 37° C. The amount of the absorbance change for 120 minutes was plotted with respect to the concentrations of the standard substance. The obtained straight line well-dependent on the concentration is shown in FIG. 14.

Example 9

Assay of β-Galactosidase by Two-Step Method using 3α-Hydroxy-17β-Methoxy-5β-Androstane β-D-Galactoside Reaction Test Solution A 0.1 M phosphate buffer solution (pH 7.5); 4 mM $MgCl_2$; 0.1 mM 3α-hydroxy-17β-methoxy-5β-androstane β-D-galactoside Reaction Test Solution B 0.1 M pyrophosphate buffer solution (pH 9.8); 1.2 mM thio-NAD; 1 mM NADH; 40 U/mL 3α-hydroxysteroid dehydrogenase Sample 1, 4, 10, 40, 100 and 200 pg/mL β-galactosidase (final concentration: 0.5, 2, 5, 20, 50 and 100 pg/mL)

Method for Assay

Figure 15:
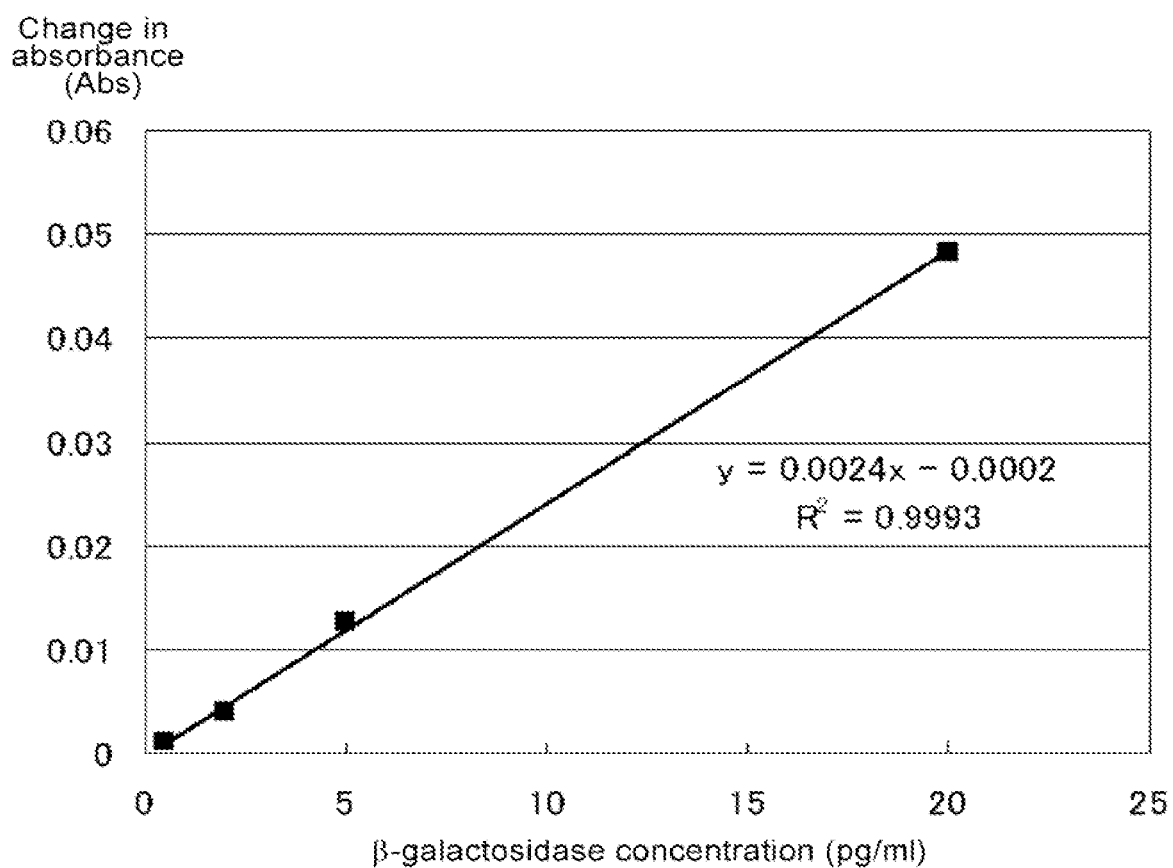
FIG. 15 is the calibration curve of β-galactosidase obtained in Example 9.

To a flat-bottomed microplate well, 25 μL of a phosphate buffer solution (pH 7.5) containing the standard substance (β-galactosidase) in a range of 0 to 200 pg/mL was added, and subsequently, 25 μL of Reaction Test Solution A was added to the well, respectively. The reaction solution was mixed, and the microplate was incubated at 37° C. for 60 minutes. Then, 50 μl of Reaction Test Solution B was added to each well, respectively, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 15.

Examples of measurements of Pumilio using androsterone β-D-galactoside are described below. However, there is no antibody that has antigen-specific reactivity and is directly labeled with β-galactosidase, and thus Labeled StreptAvidin-Biotin (LSAB) method is tried.

Reference Example 6

Manufacture of Biotin-Labeled Antibody

A biotin-labeled antibody was prepared from a biotin-labeling-kit (DOJINDO LABORATORIES) using 50 pg of F(ab')$_2$ obtained in Reference Example 1.

Example 10

Figure 16:
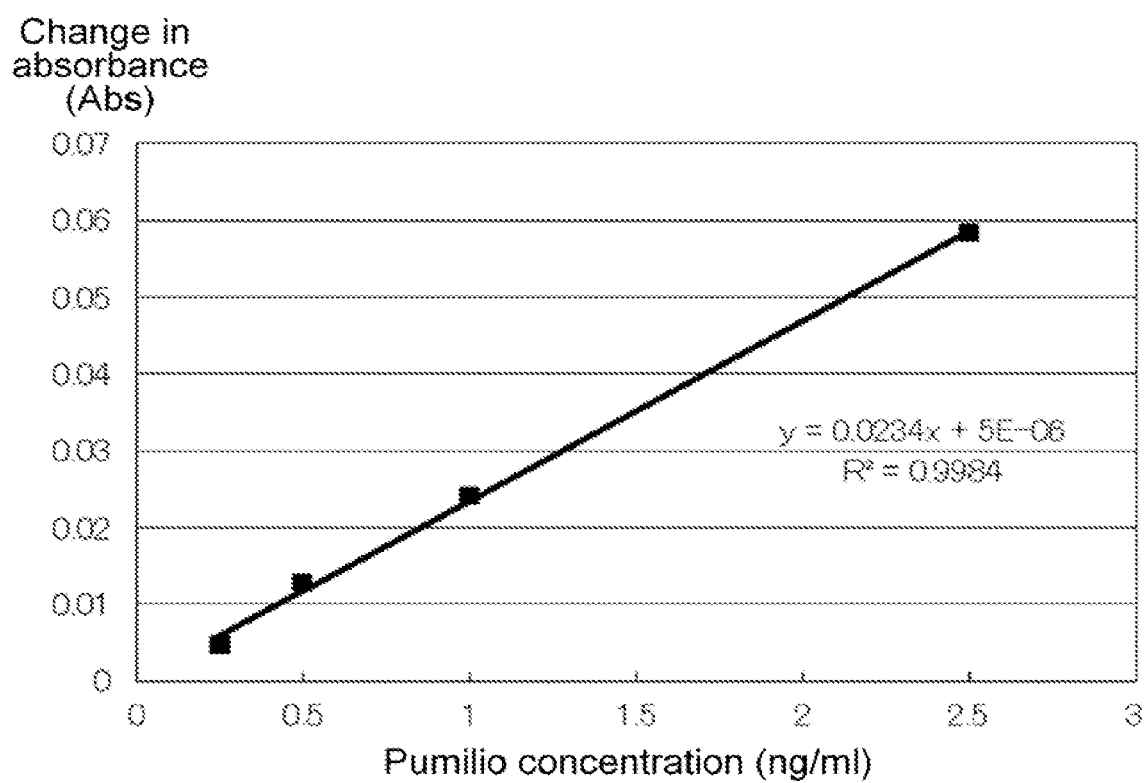
FIG. 16 is the calibration curve of Pumilio obtained in Example 10.

Assay of Pumilio by One Step Method using 5β-Androsterone β-D-Galactoside
Reaction Test Solution
0.1 M phosphate buffer solution (pH 7.7); 5 mM MgCl$_2$; 1.2 mM thio-NAD; 0.8 mM NADH; 0.05 mM 5-β-androstane β-D-galactoside
Sample
0.05, 0.1, 0.25, 0.5, 1 and 2.5 ng/ml Pumilio
Method for Assay
To a microplate immobilized with the anti-Pumilio guinea pig polyclonal antibody prepared with the method of Reference Example 5, 50 μL of TBS (pH 7.5) containing 0.1% BSA solution containing purified Pumilio (the standard substance) in a range of 0 to 2.5 ng/mL was added, and the microplate was stirred at room temperature for 2 hours. Then, the solution in the well was removed with suction, and then the well was washed with TBS (pH 7.5) containing 0.5% Triton X-100, and added with 50 μL of TBS (pH 7.5) containing 0.1% BSA solution containing the biotin-labeled anti-Pumilio mouse monoclonal antibody prepared in the method of Reference Example 6 in a concentration of approximately 0.1 pg/ml, and the microplate was stirred at room temperature for 1 hour. The solution in the well was removed with suction, and then the well was washed with TBS (pH 7.5) containing 0.5% Triton X-100, and added with 50 μL of TBS (pH 7.5) containing 0.1% BSA solution containing β-galactosidase-labeled streptavidin (F. Hoffmann-La Roche Ltd) in a concentration of 0.1 U conjugate/mL, and stirred at room temperature for 30 minutes. The solution in the well was removed with suction, and then the well was washed with TBS (pH 7.5) containing 0.5% Triton X-100, and further washed with TBS. Then, to each well, 50 μL of the Reaction Test Solution was added, respectively, and the absorbance was measured for 60 minutes using a 405 nm filter with a microplate reader (MTP-500 manufactured by CORONA CORPORATION) while warming the microplate to 37° C. The amount of the absorbance change for 60 minutes was plotted with respect to the concentrations of the standard substance. The obtained straight line well-dependent on the concentration is shown in FIG. 16.

Example 11

Figure 17:
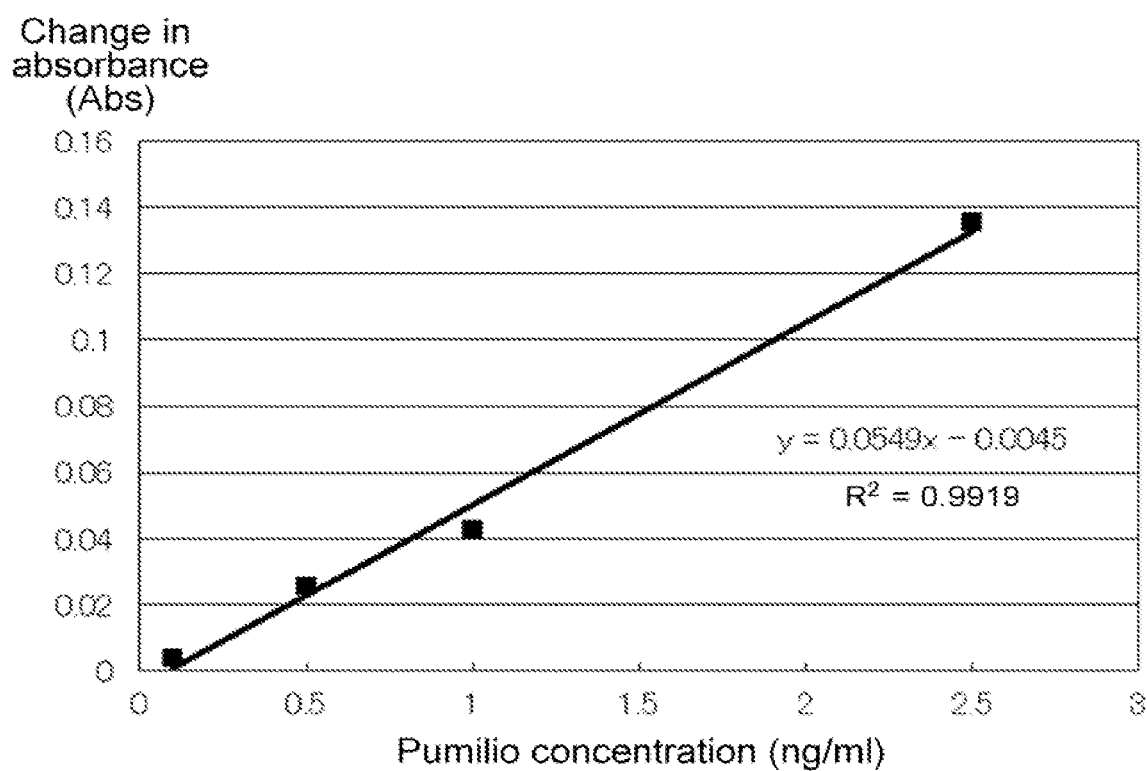
FIG. 17 is the calibration curve of Pumilio obtained in Example 11.

Assay of Pumilio by Two-Step Method using 5-β-Androsterone β-D-Galactoside
0.1 M phosphate buffer solution (pH 7.5); 0.1 mM MgCl$_2$; 0.05 mM 5β-androsterone β-D-galactoside
Reaction Test Solution A
Reaction Test Solution B
0.1 M pyrophosphate buffer solution (pH 9.0); 3 mM thio-NAD; 2 mM NADH; 40 U/mL 3α-hydroxysteroid dehydrogenase
Sample
0.05, 0.1, 0.5, 1, 2.5 and 5 ng/ml Pumilio
Method for Assay
To a microplate immobilized with the anti-Pumilio guinea pig polyclonal antibody prepared with the method of Reference Example 5, 50 μL of TBS (pH 7.5) containing 0.1% BSA solution containing purified Pumilio (the standard substance) in a range of 0 to 5 ng/ml was added, and the microplate was stirred at room temperature for 2 hours. Then, the solution in the well was removed with suction, and then the well was washed with TBS (pH 7.5) containing 0.5% Triton X-100, and added with 50 μL of TBS (pH 7.5) containing 0.1% BSA solution containing the biotin-labeled anti-Pumilio mouse monoclonal antibody prepared with the method of Reference Example 6 in a concentration of approximately 0.1 μg/ml, and the microplate was stirred at room temperature for 1 hour. The solution in the well was removed with suction, and then the well was washed with TBS (pH 7.5) containing 0.5% Triton X-100, and added with 50 μL of TBS (pH 7.5) containing 0.1% BSA solution containing β-galactosidase-labeled streptavidin (F. Hoffmann-La Roche Ltd) in a concentration of 0.1 U conjugate/mL, and stirred at room temperature for 30 minutes. The solution in the well was removed with suction, and then the well was washed with TBS (pH 7.5) containing 0.5% Triton X-100, and further washed with TBS. Then, to each well, 50 μl of Reaction Test Solution A was added, respectively, and the microplate was incubated at 37° C. for 30 minutes. Subsequently, 50 μL of Reaction Test Solution B was added to the well, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 17.

Example 12

Assay of Pumilio by One Step Method using 3α-Hydroxy-17β-Methoxy-5β-Androstane β-D-Galactoside
Reaction Test Solution
0.1 M phosphate buffer solution (pH 8.5); 1.2 mM thio-NAD; 0.8 mM NADH; 0.05 mM 3α-hydroxy-17β-methoxy-5β-androstane β-D-galactoside; 20 U/mL 3α-hydroxysteroid dehydrogenase
Sample
0.1, 0.5, 1, 2.5, 5, and 10 ng/ml Pumilio
Method for Assay
To a microplate immobilized with the anti-Pumilio guinea pig polyclonal antibody prepared with the method of Reference Example 5, 50 μL of TBS (pH 7.5) containing 0.1%

Figure 18:
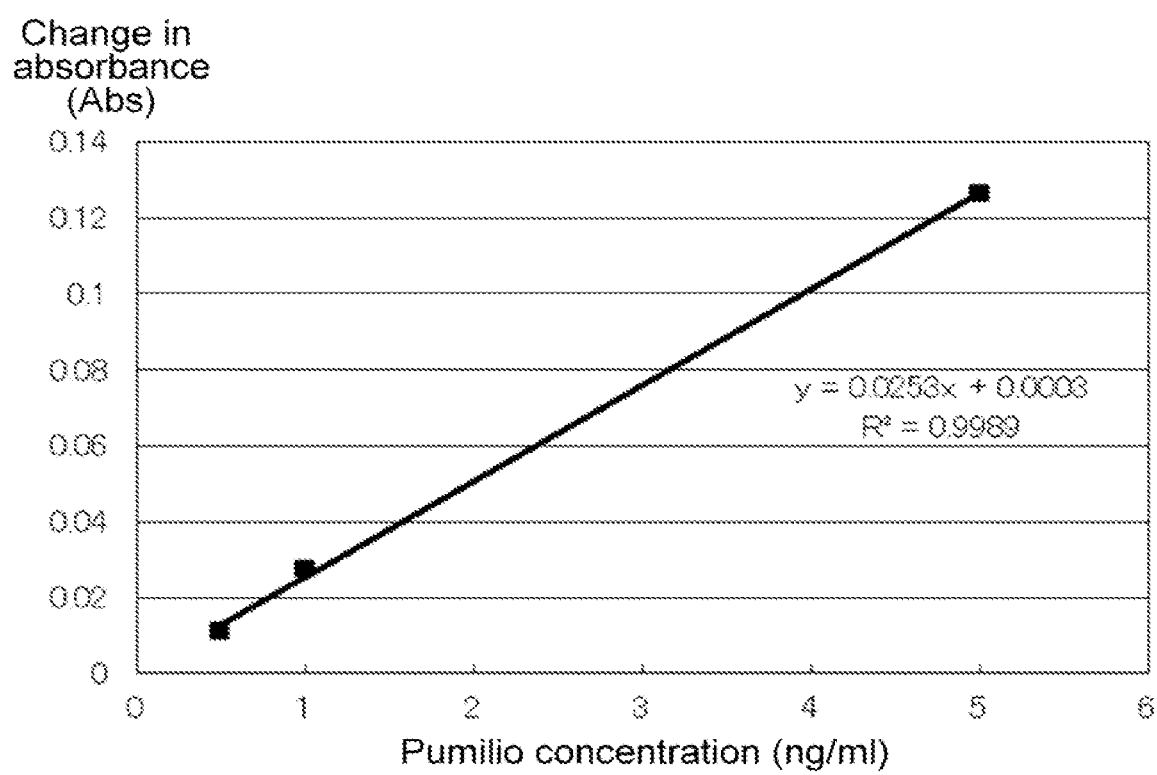
FIG. 18 is the calibration curve of Pumilio obtained in Example 12; 11.

BSA solution containing purified Pumilio (the standard substance) in a range of 0 to 10 ng/mL was added, and the microplate was stirred at room temperature for 2 hours. Then, the solution in the well was removed with suction, and then the well was washed with TBS (pH 7.5) containing 0.5% Triton X-100, and added with 50 µL of TBS (pH 7.5) containing 0.1% BSA solution containing the biotin-labeled anti-Pumilio mouse monoclonal antibody prepared in the method of Reference Example 6 in a concentration of approximately 0.1 µg/mL, and the microplate was stirred at room temperature for 1 hour. The solution in the well was removed with suction, and then the well was washed with TBS (pH 7.5) containing 0.5% Triton X-100, and added with 50 µL of TBS (pH 7.5) containing 0.1% BSA solution containing β-galactosidase-labeled streptavidin (F. Hoffmann-La Roche Ltd) in a concentration of 0.1 U conjugate/ml, and stirred at room temperature for 30 minutes. The solution in the well was removed with suction, and then the well was washed with TBS (pH 7.5) containing 0.5% Triton X-100, and further washed with TBS. Then, to each well, 50 µL of the reaction test solution was added, respectively, and the absorbance was measured for 60 minutes using a 405 nm filter with a microplate reader (MTP-500 manufactured by CORONA CORPORATION) while warming the microplate to 37° C. The amount of the absorbance change for 60 minutes was plotted with respect to the concentrations of the standard substance. The obtained straight line well-dependent on the concentration is shown in FIG. 18.

Example 13

Figure 19:
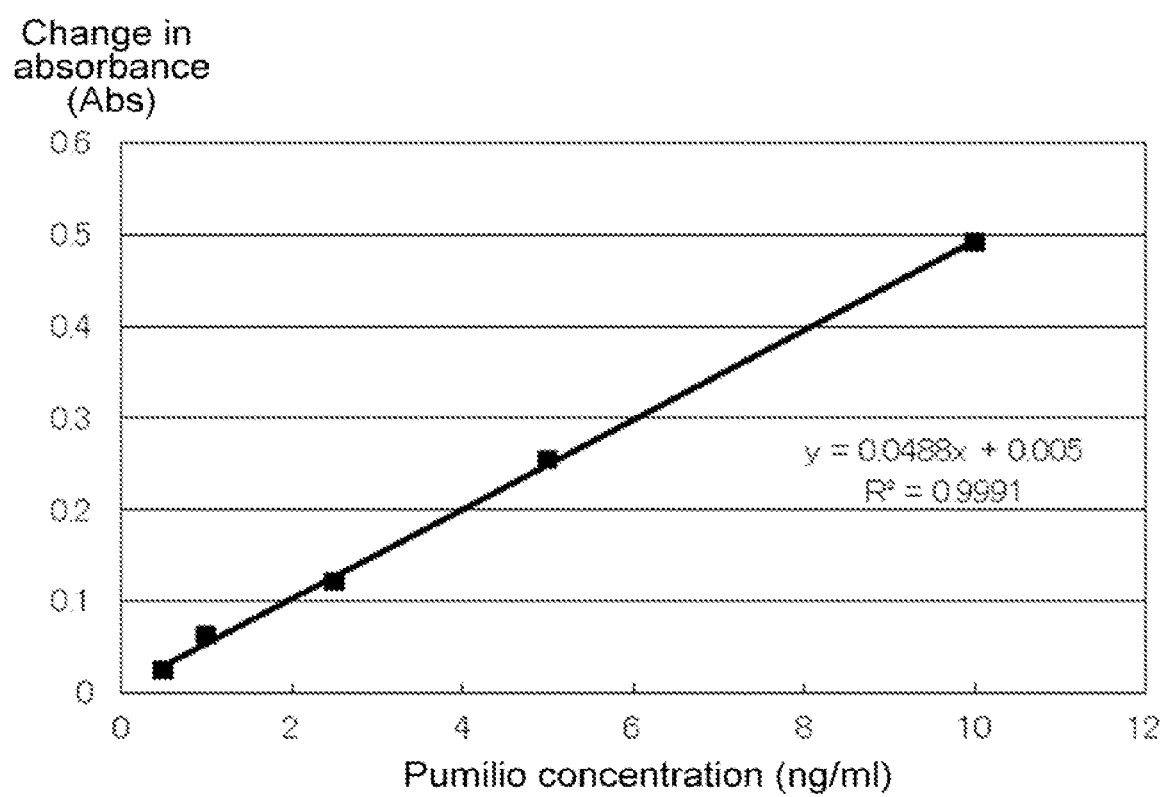
FIG. 19 is the calibration curve of Pumilio obtained in Example 13.

Assay of Pumilio by Two-Step Method using 3α-Hydroxy-17β-Methoxy-5β-Androstane β-D-Galactoside
Reaction Test Solution A
0.1 M phosphate buffer solution (pH 7.0); 0.05 mM 3α-hydroxy-17β-methoxy-5β-androstane β-D-galactoside
Reaction Test Solution B
0.1 M pyrophosphate buffer solution (pH 9.0); 2.4 mM thio-NAD; 40 U/mL 3α-hydroxysteroid dehydrogenase
Sample
0.25, 0.5, 1, 2.5, 5, 10 ng/ml Pumilio
Method for Assay
To a microplate immobilized with the anti-Pumilio guinea pig polyclonal antibody prepared with the method of Reference Example 5, 50 µL of TBS (pH 7.5) containing 0.1% BSA solution containing purified Pumilio (the standard substance) in a range of 0 to 10 ng/mL was added, and the microplate was stirred at room temperature for 2 hours. Then, the solution in the well was removed with suction, and then the well was washed with TBS (pH 7.5) containing 0.5% Triton X-100, and 50 µL of TBS (pH 7.5) containing 0.1% BSA solution containing the biotin-labeled anti-Pumilio mouse monoclonal antibody prepared with the method of Reference Example 6 in a concentration of approximately 0.3 µg/mL was added, and the microplate was stirred at room temperature for 1 hour. The solution in the well was removed with suction, and then the well was washed with TBS (pH 7.5) containing 0.5% Triton X-100, and added with 50 µL of TBS (pH 7.5) containing 0.1% BSA solution containing β-galactosidase-labeled streptavidin (F. Hoffmann-La Roche Ltd) in a concentration of 0.1 U conjugate/mL, and stirred at room temperature for 30 minutes. The solution in the well was removed with suction, and then the well was washed with TBS (pH 7.5) containing 0.5% Triton X-100, and further washed with TBS. Then, 50 µL of Reaction Test Solution A was added to each well, respectively, and the microplate was incubated at 37° C. for 60 minutes. Subsequently, to the well, 50 µL of Reaction Test Solution B was added, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 19.

Reference Example 7

Figure 20:
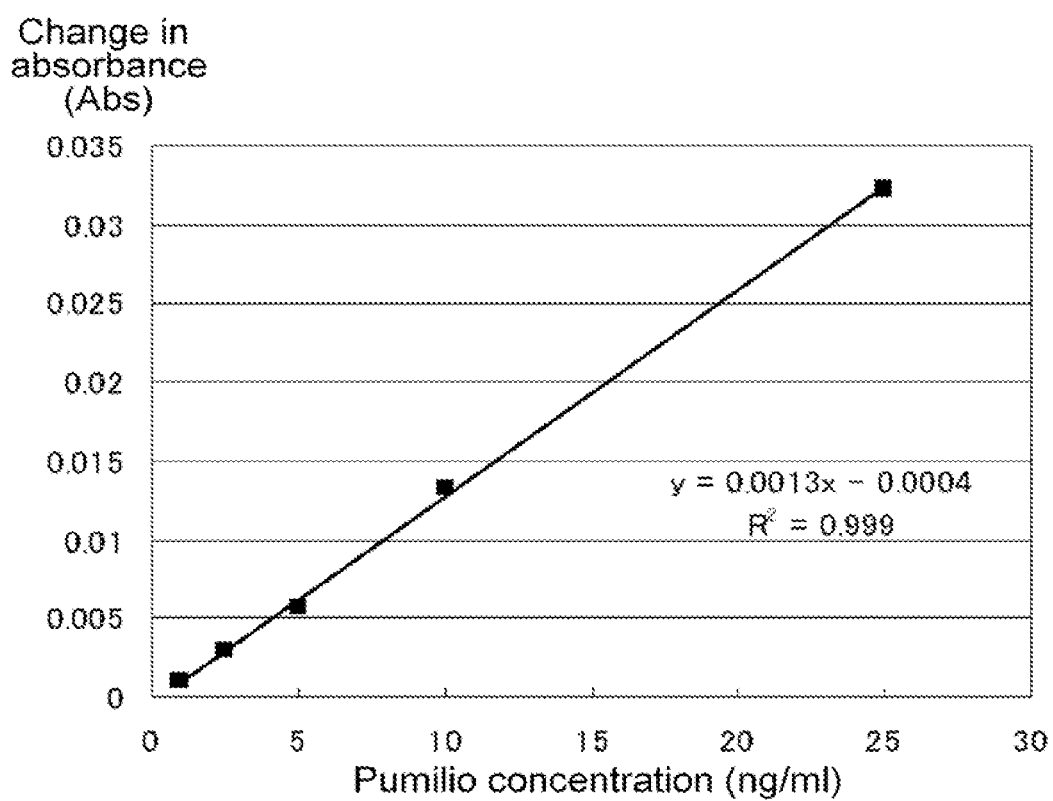
FIG. 20 is the calibration curve of Pumilio obtained in Reference Example 7.

Assay of Pumilio using p-Nitrophenyl Phosphate (p-NPP)
Reaction Test Solution
0.1 M glycine buffer solution (pH 10.3); 1 mM $MgCl_2$; 1 mM $ZnCl_2$; 1 mg/ml p-NPP
Sample for Assay
0, 1, 2.5, 5, 10 and 25 ng/ml Pumilio
Method for Assay
To a microplate immobilized with the anti-Pumilio guinea pig polyclonal antibody prepared with the method of Reference Example 3, 50 µL of TBS (pH 7.5) containing 0.1% BSA solution containing purified Pumilio (the standard substance) in a range of 0 to 25 ng/mL was added, and the microplate was stirred at room temperature for 1 hour. Then, the solution in the well was removed with suction, and then the microplate was washed with TBS (pH 7.5) containing 0.05% Tween 20. 50 µL of TBS (pH 7.5) containing 0.1% BSA solution containing the ALP-labeled anti-Pumilio mouse monoclonal antibody prepared with the method of Reference Example in a concentration of 1 µg/mL was added, and the microplate was stirred for 1 hour. The solution in the well was removed with suction, and then the microplate was washed with TBS (pH 7.5) containing 0.05% Tween 20. 100 µL of the reaction test solution was added to each well, and the absorbance was measured for 30 minutes using a 405 nm filter with a microplate reader (MTP-500 manufactured by CORONA CORPORATION) while warming the microplate to 37° C. The amount of the absorbance change for 30 minutes was plotted with respect to the concentrations of the standard substance. The obtained straight line well-dependent on the concentration is shown in FIG. 20.

Reference Example 8

Figure 21:
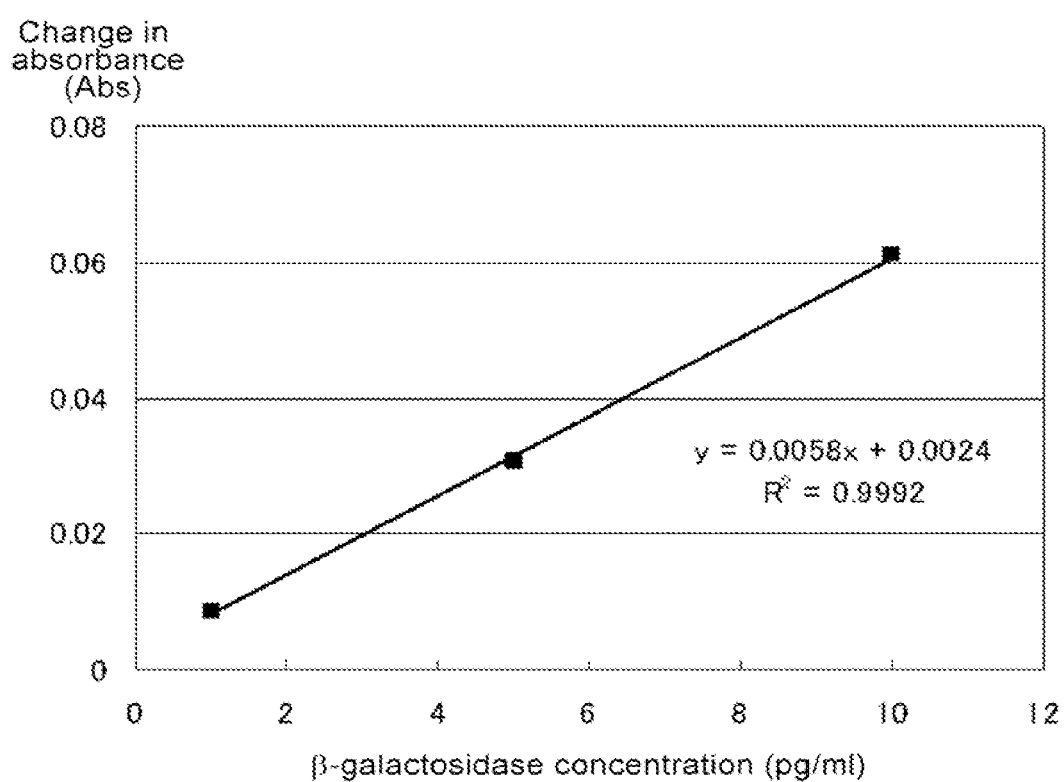
FIG. 21 is the calibration curve of β-galactosidase obtained in Reference Example 8.

Assay of β-Galactosidase using o-Nitrophenyl β-D-Galactopyranoside (ONPG)
Reaction Test Solution
0.1 M phosphate buffer solution (pH 7.3); 0.2 mM 2-mercaptoethanol; 1 mM $MgCl_2$; 10 mM ONPG
Sample for Assay
2, 10, 20 and 50 ng/mL β-galactosidase (final concentration: 1, 5, 10, and 25 ng/mL)
Method for Assay
To a flat-bottomed microplate well, 50 µL of a phosphate buffer solution (pH 7.3) containing the standard substance (β-galactosidase) in a range of 0 to 25 ng/mL was added, and subsequently, to the well, 50 µL of the reaction test solution was added, respectively, and the absorbance was measured for 60 minutes using a 415 nm filter with a microplate reader (MTP-500 manufactured by CORONA CORPORATION) while warming the microplate to 37° C. The amount of the absorbance change for 60 minutes was plotted with respect to the concentrations of the standard substance. The obtained straight line well-dependent on the concentration is shown in FIG. 21.

Calculation Method of Detection Limit and Quantification Limit

The amount of the absorbance change of each measurement result is plotted with respect to the concentrations of the standard substance, and only the concentrations in parallel on the straight line are extracted to prepare a fitted curve. Then, the standard deviation of the blank (not including the standard substance; n≥3) is calculated, and the 3-fold value and 10-fold value thereof are divided by the slope of the fitted curve, and the obtained numerical values are taken as the detection limit and the quantification limit, respectively. The detection limit and the quantification limit calculated from each experiment result are summarized in Tables 3, 4 and 5.

TABLE 3

Detection limit and quantification limit of alkaline phosphatase and β-Galactosidase

| Enzyme | Substrate | Method | Detection limit | Quantification limit |
|---|---|---|---|---|
| ALP | 17-OMe 5β-A3P | One-step | $3.25 \times 10^{-18}$ | $1.08 \times 10^{-17}$ |
| | | Two-steps | $8.19 \times 10^{-20}$ | $2.73 \times 10^{-19}$ |
| β-Gal | 5α-AG | Two-steps | $3.89 \times 10^{-19}$ | $1.3 \times 10^{-18}$ |
| | 5β-AG | One-step | $3.31 \times 10^{-19}$ | $1.1 \times 10^{-18}$ |
| | | Two-steps | $7.48 \times 10^{-20}$ | $2.49 \times 10^{-19}$ |
| | 17-OMe 5β-AG | One-step | $3.21 \times 10^{-19}$ | $1.07 \times 10^{-18}$ |
| | | Two-steps | $1.09 \times 10^{-19}$ | $3.64 \times 10^{-19}$ |
| | ONPG | | $4.5 \times 10^{-17}$ | $1.5 \times 10^{-16}$ |
| | 4-MUG | | $9.76 \times 10^{-18}$ | $3.25 \times 10^{-17}$ |

ALP and β-Gal Assay (unit: mol)

TABLE 4

Detection limit and quantification limit of Pumilio protein (β-Galactosidase system) ELISA Assay (unit: mol)

| | | Detection limit | Quantification limit |
|---|---|---|---|
| 5β-AG | One-step | $2.21 \times 10^{-17}$ | $7.35 \times 10^{-17}$ |
| | Two-steps | $1.65 \times 10^{-17}$ | $5.51 \times 10^{-17}$ |
| 17-OMe 5β-AG | One-step | $3.24 \times 10^{-17}$ | $1.08 \times 10^{-16}$ |
| | Two-steps | $3.17 \times 10^{-17}$ | $1.06 \times 10^{-16}$ |
| 4-MUG | | $2.07 \times 10^{-16}$ | $6.91 \times 10^{-16}$ |

TABLE 5

Detection limit and quantification limit of Pumilio protein (Alkaline phosphatase system) ELISA Assay

| Substrate | | Detection limit | Quantification limit |
|---|---|---|---|
| 5α-A3P | One-step | $3.57 \times 10^{-14}$ | $7.3 \times 10^{-14}$ |
| | Two-steps | $2.63 \times 10^{-16}$ | $8.76 \times 10^{-16}$ |
| 5β-A3P | One-step | $3.96 \times 10^{-15}$ | $1.32 \times 10^{-14}$ |
| | Two-steps | $1.2 \times 10^{-16}$ | $4 \times 10^{-16}$ |
| 17-OMe 5β-A3P | One-step | $4.0 \times 10^{-17}$ | $1.3 \times 10^{-16}$ |
| | Two-steps | $2.45 \times 10^{-18}$ | $8.17 \times 10^{-18}$ |
| p-NPP | | $3.97 \times 10^{-16}$ | $1.32 \times 10^{-15}$ |

Example 14

Assay of Horseradish Peroxidase by One Step Method using 3α-Tert-Butyl-Peroxy-5β-Androsterone 3α-tert-butyl-peroxy-5β-androsterone

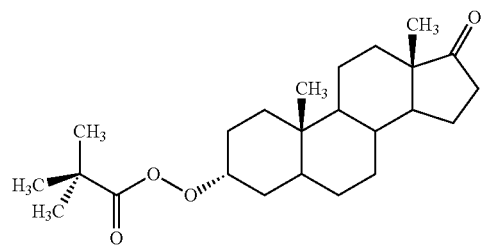

Synthesis of 3α-Tert-Butyl-Peroxy-5β-Androsterone

3α-chloro-5β-androsterone (100 mg) was dissolved in a dichloromethane solution (15 mL), to prepare the reaction test solution. To the present solution, a solution of tert-butyl-hydroperoxide (30 mg) dissolved in an aqueous solution (15 mL) of 20% sodium hydroxide was added, and the reaction solution was reacted with stirring at room temperature for 2 hours. The organic layer was collected from the reaction solution, and washed with an aqueous solution of saturated sodium hydrogen carbonate and saturated saline, sequentially. The organic layer was dehydrated with anhydrous sodium sulfate, and then the solvent was distilled off under reduced pressure. The residue was purified with silica gel chromatography (24×240 mm, 10% methanol-chloroform), and then 88 mg of the present compound was obtained. Identification of the present compound was performed from $^1$H-NMR, ESI-HR-MS and m.p. (melting point).

Reaction Test Solution 0.1 M phosphate buffer solution (pH 7.0); 10 mM $MgCl_2$; 6 mM thio-NAD; 1 mM NADH; 0.1 mM 3α-tert-butyl-peroxy-5β-androsterone; 40 U/mL 3α-hydroxysteroid dehydrogenase Sample 5, 10, 25, 50, 100 and 250 pg/mL horseradish peroxidase (final concentration: 2.5, 5, 12.5, 25, 50 and 125 pg/mL)

Method for Assay

Figure 22:
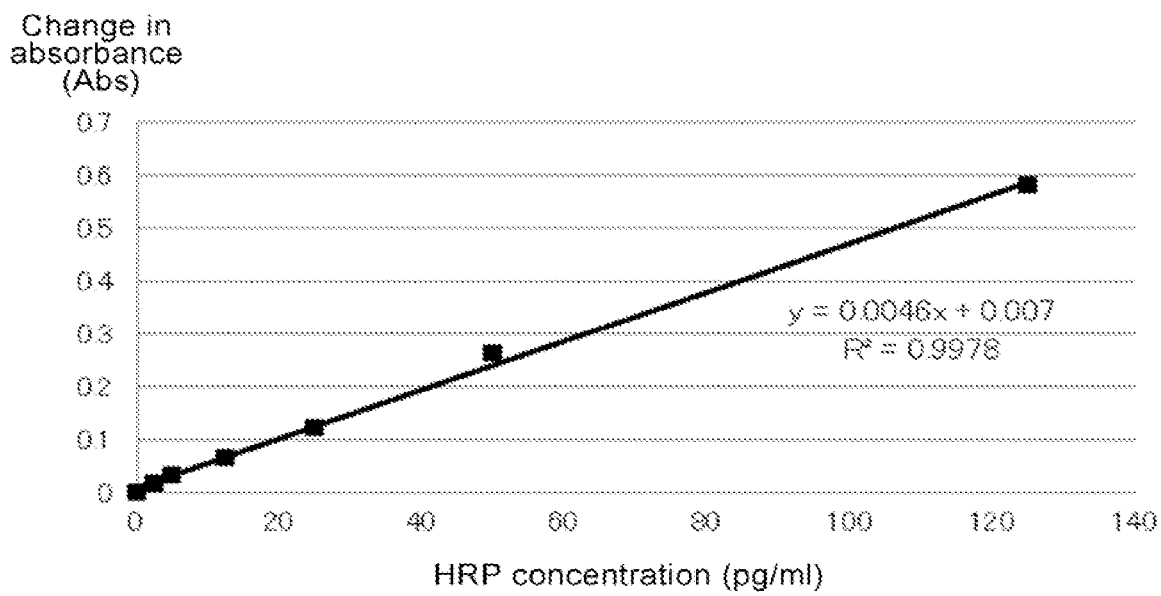
FIG. 22 is the calibration curve of horseradish peroxidase obtained in Example 14.

To a flat-bottomed microplate well, 50 μL of a phosphate buffer solution (pH 7.0) containing the standard substance (horseradish peroxidase) (referred to as HRP below) in a range of 0 to 250 pg/mL was added, and subsequently, to the well, 50 μL of the Reaction Test Solution was added, respectively, and the absorbance was measured for 120 minutes using a 405 nm filter with a microplate reader (MTP-500 manufactured by CORONA CORPORATION) while warming the microplate to 37° C. The amount of the absorbance change for 120 minutes was plotted with respect to the concentrations of the standard substance. The obtained straight line well-dependent on the concentration is shown in FIG. 22.

Example 15

Assay of Pumilio by One Step Method using 3α-Tert-Butyl-Peroxy-5β-Androsterone

Figure 23:
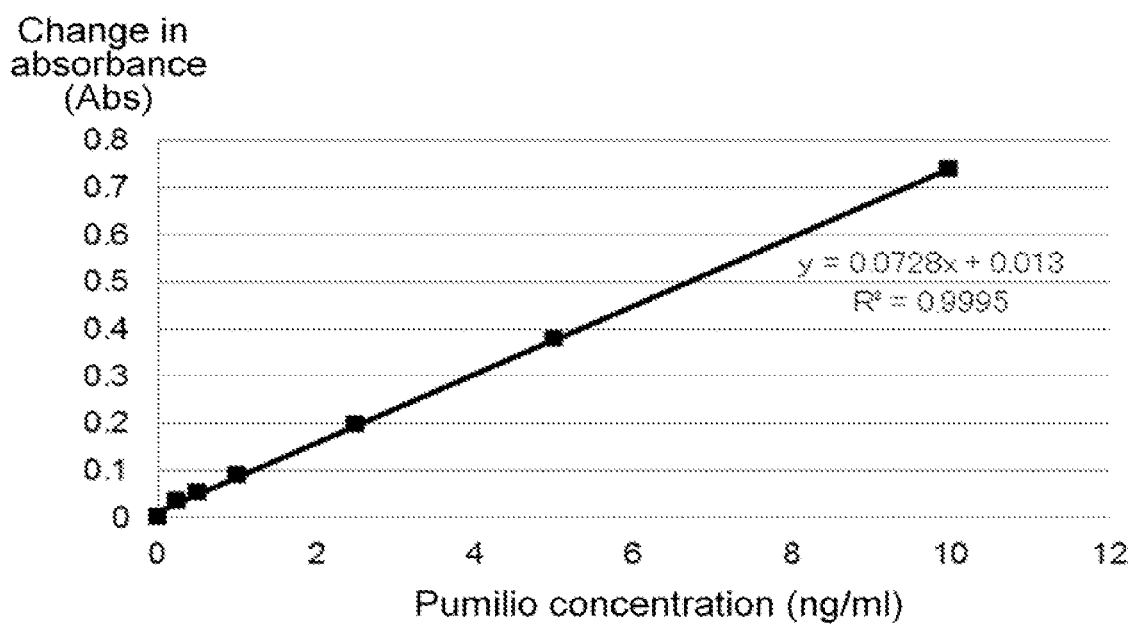
FIG. 23 is the calibration curve of Pumilio obtained in Example 15.

Reaction Test Solution 0.1 M phosphate buffer solution (pH 7.0); 10 mM $MgCl_2$; 6 mM thio-NAD; 1 mM NADH; 0.1 mM 3α-tert-butyl-peroxy-5β-androsterone; 40 U/mL 3α-hydroxysteroid dehydrogenase Sample
0.05, 0.1, 0.25, 0.5, 1 and 2.5 ng/ml Pumilio
Method for Assay To a microplate immobilized with the anti-Pumilio guinea pig polyclonal antibody prepared with the method of Reference Example 5, 50 μL of TBS (pH 7.5) containing 0.1% BSA solution containing purified Pumilio (the standard substance) in a range of 0 to 2.5 ng/mL was added, and the microplate was stirred at room temperature for 2 hours. Then, the solution in the well was removed with suction, and then the well was washed with TBS (pH 7.5) containing 0.5% Triton X-100. 50 μL of TBS (pH 7.5) containing 0.1% BSA solution containing the HRP-labeled anti-Pumilio mouse monoclonal antibody in a concentration of approximately 0.1 μg/mL was added, and the microplate was stirred at room temperature for 1 hour. The solution in the well was removed with suction, and then the well was washed with TBS (pH 7.5) containing 0.5% Triton X-100. Then, to each well, 50 μL of the reaction test solution was added, respectively, and the absorbance was measured for 60 minutes using a 405 nm filter with a microplate reader (MTP-500 manufactured by CORONA CORPORATION) while warming the microplate to 37° C. The amount of the absorbance change for 60 minutes was plotted with respect to the concentrations of the standard substance. The obtained straight line well-dependent on the concentration is shown in FIG. 23.

Synthesis of 3α-Benzoyl-Peroxy-5β-Androsterone and 3α-Acetyl-Peroxy-5β-Androsterone The titled compounds were obtained similarly to the synthesis of 3α-tert-butyl-peroxy-5β-androsterone described in Example 14 except that tert-butyl-hydroperoxide was changed to benzoyl-hydroperoxide or acetyl-hydroperoxide.

3α-Benzoyl-Peroxy-5β-Androsterone

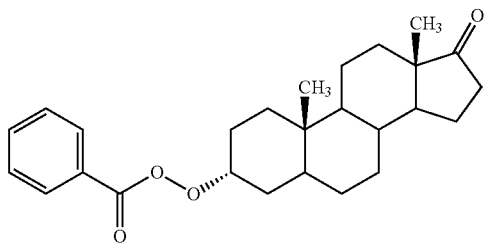 [SMILES: C[C@]12CC[C@@H](OOC(=O)c3ccccc3)CC1CCC1C2CC[C@]2(C)C(=O)CCC12]

3α-Acetyl-Peroxy-5β-Androsterone

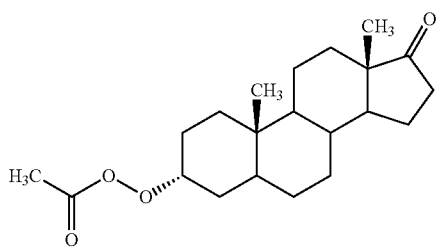 [SMILES: CC(=O)OO[C@@H]1CC[C@@]2(C)C(CCC3C2CC[C@]2(C)C(=O)CCC32)C1]

INDUSTRIAL APPLICABILITY

The present invention can be suitably used in the field of clinical examination or the field of food examination that demands high sensitivity and simple measurement.

What is claimed is:

1. A kit for immunoassay of a target protein antigen employing enzymatic labeling comprising reagents (1) to (5) described below:
   (1) alkaline phosphatase labeled with an antibody specific to a target protein antigen,
   (2) an androsterone derivative represented by the formula (1), which is a substrate of the enzyme described above

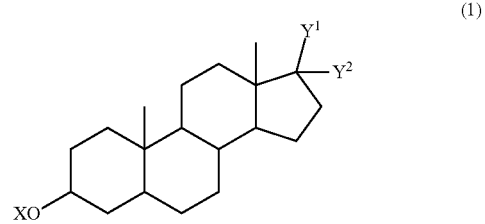

wherein, X represents a phosphate group, $Y^1$ represents hydrogen, and $Y^2$ represents a $C_1$ alkoxy group,
   (3) hydroxysteroid dehydrogenase (HSD),
   (4) NADH and/or NADPH, and
   (5) thio-NAD and/or thio-NADP.

2. A kit for enzyme immunoassay comprising reagents (1) to (5) below:
   (1) glucosidase, galactosidase, fructosidase or mannosidase which is labeled with an antibody specific to a target protein antigen,
   (2) an androsterone derivative represented by the formula (1), which is a substrate of the enzyme described above

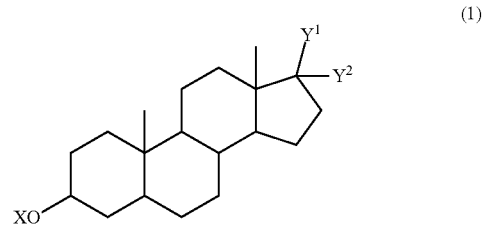

wherein, X represents a sugar moiety, the sugar moiety represents one selected from the group consisting of glucose, galactose, fructose and mannose, and $Y^1$ represents hydrogen, and $Y^2$ represents a $C_1$ alkoxy group,
   (3) hydroxysteroid dehydrogenase (HSD),
   (4) NADH and/or NADPH, and
   (5) thio-NAD and/or thio-NADP.

3. A kit for enzyme immunoassay comprising reagents (1) to (5) below:
   (1) peroxidase labeled with an antibody specific to a target protein antigen,
   (2) an androsterone derivative represented by the formula (1), which is a substrate of the enzyme described above

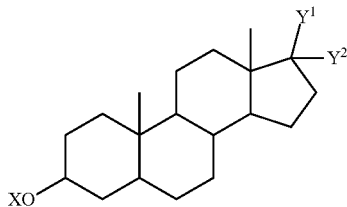

(1)

wherein, X represents —O—CO—R (provided that R represents a $C_{1-6}$ alkyl group or a phenyl group), $Y^1$ represents hydrogen, and $Y^2$ represents a $C_1$ alkoxy group,
(3) hydroxysteroid dehydrogenase (HSD),
(4) NADH and/or NADPH, and
(5) thio-NAD and/or thio-NADP.

4. A kit for assaying a nucleic acid probe comprising reagents (1) to (5) below:
(1) alkaline phosphatase labeled with a nucleic acid probe specifically binding to a target nucleic acid,
(2) an androsterone derivative represented by the formula (1), which is a substrate of the enzyme described above

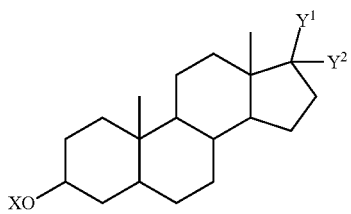

(1)

wherein, X represents a phosphate group, $Y^1$ represents hydrogen, and $Y^2$ represents a $C_1$ alkoxy group,
(3) hydroxysteroid dehydrogenase (HSD),
(4) NADH and/or NADPH, and
(5) thio-NAD and/or thio-NADP.

5. A kit for assaying a nucleic acid probe comprising reagents (1) to (5) below:
(1) glucosidase, galactosidase, fructosidase or mannosidase labeled with a nucleic acid probe specifically binding to a target nucleic acid,
(2) an androsterone derivative represented by the formula (1), which is a substrate of the enzyme described above

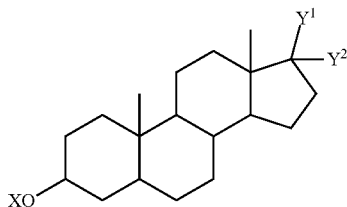

(1)

wherein, X represents a sugar moiety, the sugar moiety represents one selected from the group consisting of glucose, galactose, fructose and mannose, and $Y^1$ represents hydrogen, and $Y^2$ represents a $C_1$ alkoxy group,
(3) hydroxysteroid dehydrogenase (HSD),
(4) NADH and/or NADPH, and
(5) thio-NAD and/or thio-NADP.

6. A kit for assaying a nucleic acid probe comprising reagents (1) to (5) below:
(1) peroxidase labeled with a nucleic acid probe specifically binding to a target nucleic acid,
(2) an androsterone derivative represented by the formula (1), which is a substrate of the enzyme described above

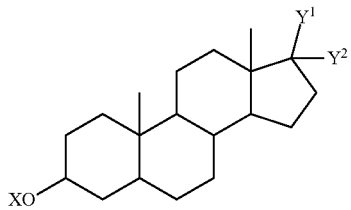

(1)

wherein, X represents —O—CO—R (provided that R represents a $C_{1-6}$ alkyl group or a phenyl group), $Y^1$ represents hydrogen, and $Y^2$ represents a $C_1$ alkoxy group,
(3) hydroxysteroid dehydrogenase (HSD),
(4) NADH and/or NADPH, and
(5) thio-NAD and/or thio-NADP.

7. An androsterone derivative represented by the formula (1) below:

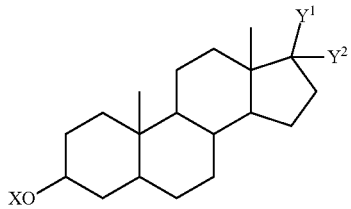

(1)

(A) X represents a phosphate group, $Y^1$ represents hydrogen, and $Y^2$ represents $C_1$ alkoxy group,
(B) X represents one of a sugar moiety selected from the group consisting of glucose, galactose, fructose and mannose, $Y^1$ represents hydrogen, and $Y^2$ represents a $C_1$ alkoxy group,
(C) X represents —O—CO—R, R represents a $C_{1-6}$ alkyl group or a phenyl group, $Y^1$ represents hydrogen, and $Y^2$ represents a $C_1$ alkoxy group, wherein the androsterone derivative is useful for immunoassay of a target protein antigen employing enzymatic labeling.

8. The androsterone derivative according to claim 7, wherein the definitions of X, $Y^1$ and $Y^2$ are those of (A), X represents a phosphate group, and $Y^1$ represents hydrogen, and $Y^2$ represents a $C_1$ alkoxy group.

9. The androsterone derivative according to claim 7, wherein the definitions of X, $Y^1$ and $Y^2$ are those of (B), X represents one of a sugar moiety selected from the group consisting of glucose, galactose, fructose and mannose, $Y^1$ represents hydrogen, and $Y^2$ represents a $C_1$ alkoxy group.

10. The androsterone derivative according to claim 7, wherein the definitions of X, $Y^1$ and $Y^2$ are those of (C), X represents —O—CO—R, R represents a $C_{1-6}$ alkyl group or a phenyl group, and $Y^1$ represents hydrogen, and $Y^2$ represents a $C_1$ alkoxy group.

* * * * *